United States Patent
Heaton et al.

(10) Patent No.: US 10,226,204 B2
(45) Date of Patent: Mar. 12, 2019

(54) METHOD FOR DETECTING AND RESPONDING TO FALLS BY RESIDENTS WITHIN A FACILITY

(71) Applicant: Blue Willow Systems Inc., Vancouver (CA)

(72) Inventors: Richard Heaton, San Jose, CA (US); Vikram Devdas, Vancouver (CA); Dan Erichsen, Vancouver (CA); Joe Edwards, Abbotsford (CA)

(73) Assignee: PHILIPS NORTH AMERICA LLC, Andover, MA (US)

( * ) Notice: Subject to any disclaimer, the term of this patent is extended or adjusted under 35 U.S.C. 154(b) by 0 days.

(21) Appl. No.: 15/627,186

(22) Filed: Jun. 19, 2017

(65) Prior Publication Data

US 2018/0000385 A1 Jan. 4, 2018

Related U.S. Application Data

(60) Provisional application No. 62/351,514, filed on Jun. 17, 2016.

(51) Int. Cl.
*A61B 5/11* (2006.01)
*G08B 21/04* (2006.01)
(Continued)

(52) U.S. Cl.
CPC .............. *A61B 5/1117* (2013.01); *A61B 5/01* (2013.01); *A61B 5/11* (2013.01); *A61B 5/7264* (2013.01);
(Continued)

(58) Field of Classification Search
CPC ............ A61B 5/681; A61B 2562/0219; A61B 5/0022; A61B 5/11; A61B 5/1117; A61B 5/0002; A61B 5/7264; A61B 5/7267; A61B 5/7275; A61B 5/1113; A61B 5/746; A61B 5/6825; A61B 5/6831; A61B 5/72; A61B 5/747; A61B 5/6802; A61B 5/6801;
(Continued)

(56) References Cited

U.S. PATENT DOCUMENTS

2008/0001735 A1* 1/2008 Tran ..................... G06F 19/3418
340/539.22
2016/0058330 A1* 3/2016 Menzel ................. A61B 5/1117
600/595

(Continued)

*Primary Examiner* — Benyam Haile
(74) *Attorney, Agent, or Firm* — Run8 Patent Group, LLC; Peter Miller

(57) ABSTRACT

One variation of a method for detecting and responding to falls by residents within a facility includes: at a wearable device worn by a resident, writing sensor data from a sensor integrated into the wearable device to a buffer, inputting sensor data into a compressed fall detection model—defining a compressed form of a complete fall detection model and stored locally on the wearable device—to detect a fall event at a first time, and transmitting a corpus of sensor data from the buffer and a cue for confirmation of the fall event to a local wireless hub in response to detecting the fall event; and, remotely from the wearable device, inputting the corpus of sensor data into the complete fall detection model—stored remotely from the wearable device—to confirm the fall event and dispatching a care provider to assist the resident in response to confirming the fall event.

19 Claims, 5 Drawing Sheets

(51) Int. Cl.
*A61B 5/00* (2006.01)
*A61B 5/01* (2006.01)
*H04W 4/02* (2018.01)
*G06F 19/00* (2018.01)
*G08B 25/00* (2006.01)
*G08B 25/01* (2006.01)
*G08B 29/18* (2006.01)
*G01P 15/08* (2006.01)
*G01P 15/00* (2006.01)
*H04M 3/51* (2006.01)

(52) U.S. Cl.
CPC ............ *G06F 19/00* (2013.01); *G08B 21/043* (2013.01); *G08B 21/0446* (2013.01); *G08B 25/001* (2013.01); *G08B 25/016* (2013.01); *G08B 29/186* (2013.01); *H04W 4/023* (2013.01); *A61B 5/0022* (2013.01); *G01P 15/00* (2013.01); *G01P 15/0891* (2013.01); *H04M 3/5116* (2013.01)

(58) Field of Classification Search
CPC ...... A61B 5/7221; H04W 4/023; H04L 67/22; G01P 15/00; G01P 15/0891; G08B 21/0446; H04M 2250/12; H04M 3/5116; H04M 3/42042; Y02D 70/26
See application file for complete search history.

(56) References Cited

U.S. PATENT DOCUMENTS

2016/0275771 A1\* 9/2016 Visweswara ......... A61B 5/6822
2018/0014253 A1\* 1/2018 Dai Javad ......... H04W 52/0277

\* cited by examiner

METHOD FOR DETECTING AND RESPONDING TO FALLS BY RESIDENTS WITHIN A FACILITY

CROSS-REFERENCE TO RELATED APPLICATIONS

This application claims the benefit of U.S. Provisional Application No. 62/351,514, filed on 17 Jun. 2016, which is incorporated in its entirety by this reference.

The application is related to U.S. patent application Ser. No. 15/339,771, filed on 31 Oct. 2016, which is incorporated in its entirety by this reference.

TECHNICAL FIELD

This invention relates generally to the field of senior and disabled care and more specifically to a new and useful method for detecting and responding to falls by residents within a facility in the field of senior and disabled care.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. System and Methods

Figure 1:
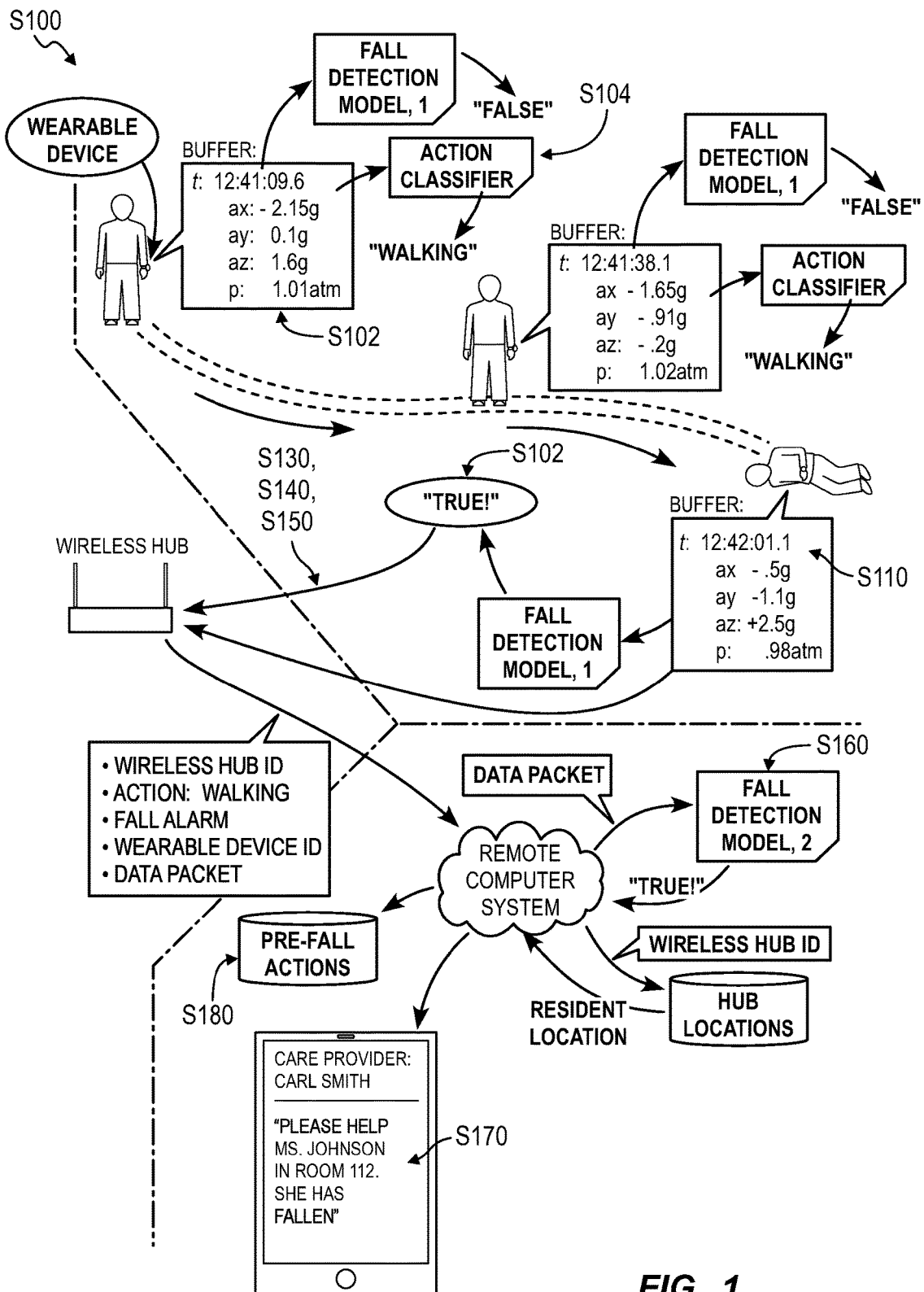
FIG. 1 is a flowchart representation of a method.

As shown in FIG. 1, a method S100 for detecting and responding to falls by residents within a facility includes, at a wearable device worn by a resident: writing sensor data from a sensor integrated into the wearable device to a buffer in Block S110; detecting a fall event in response to sensor data exceeding a first threshold value stored locally on the wearable device in Block S120; and, in response to detection of the fall event: wirelessly connecting with a local wireless hub in Block S130, transmitting a sequence of sensor data from the buffer and a cue for fall event confirmation to the wireless hub in Block S140, and wirelessly disconnecting from the wireless hub in Block S150. The method S100 also includes: remotely from the wearable device, confirming the fall event based on sensor data from the buffer exceeding a second threshold value greater than the first threshold value in Block S160; and in response to confirmation of the fall event, dispatching a care provider to a location proximal the wearable device in Block S170.

Figure 4:
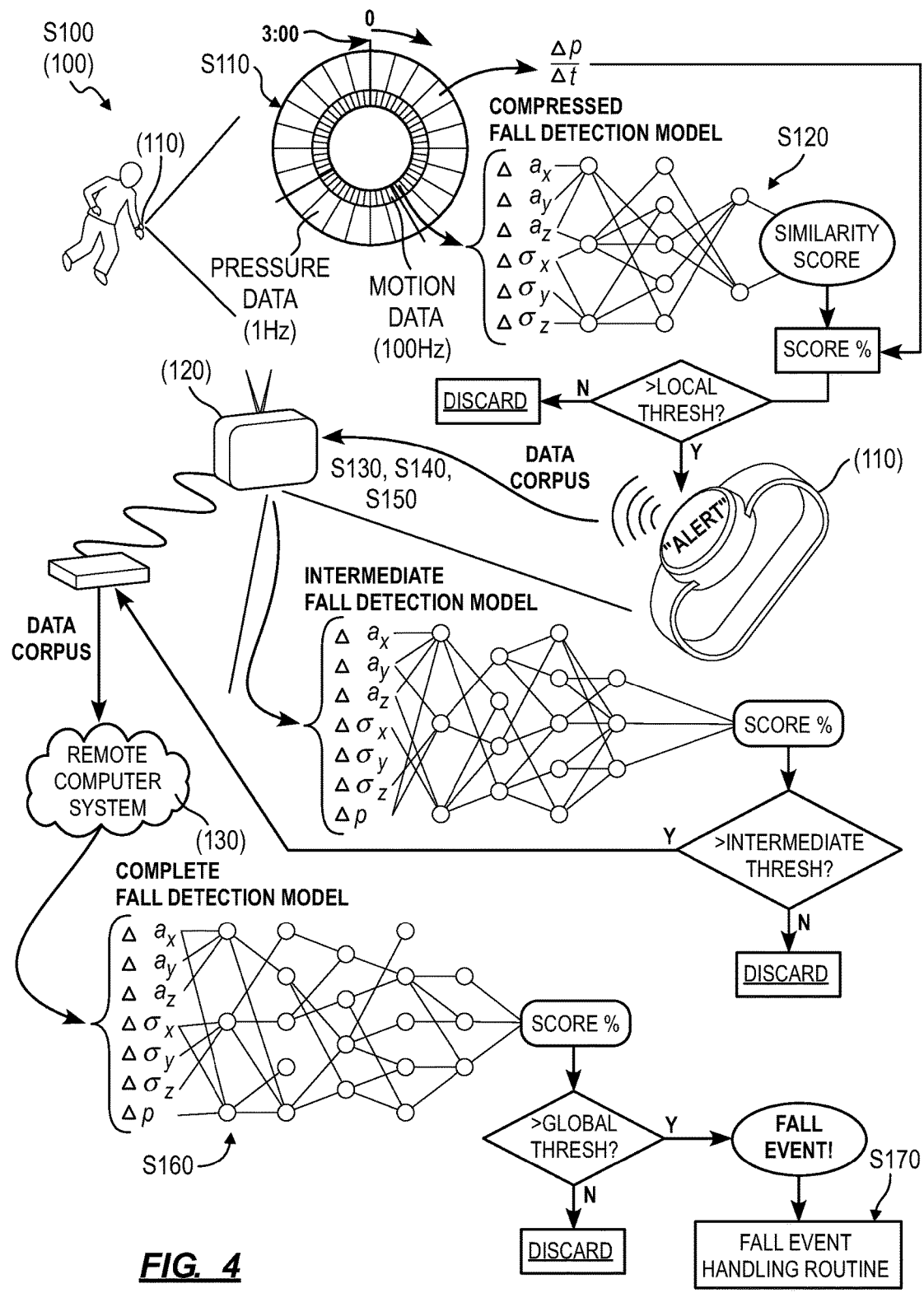
FIG. 4 is a flowchart representation of one variation of the method.

As shown in FIGS. 1 and 4, one variation of the method S100 includes, at a wearable device worn by a resident: writing sensor data from a sensor integrated into the wearable device to a buffer in Block S110; inputting sensor data read from the sensor into a compressed fall detection model stored locally on the wearable device to detect a fall event at a first time in Block S120, the compressed fall detection model defining a compressed form of a complete fall detection model; and, in response to detecting the fall event at a first time, wirelessly connecting to a local wireless hub in Block S130, transmitting a corpus of sensor data—corresponding to a duration of time terminating at approximately the first time—from the buffer and a cue for confirmation of the fall event to the wireless hub in Block S140, and wirelessly disconnecting from the wireless hub in Block S150. This variation of the method S100 also includes: remotely from the wearable device, inputting the corpus of sensor data into the complete fall detection model, stored remotely from the wearable device, to confirm the fall event in Block S160; and, in response to confirming the fall event, dispatching a care provider to assist the resident in Block S170.

As shown in FIG. 1, another variation of the method S100 includes, at a wearable device worn by a resident: during a first period of time, recording a first set of data packets to local memory in Block S102, each data packet in the set of data packets corresponding to a timestamp including values read from a sensor integrated into the wearable device during a sampling period corresponding to the timestamp; transforming data packets in the first set of data packets into an action performed by the resident in Block S104; at a second time immediately succeeding the first time, recording a second set of data packets to local memory in Block S110; detecting a fall event by passing a data packet in the second set of data packets into a fall detection model stored locally on the wearable device in Block S120; and, in response to detection of the fall event, wirelessly connecting with a local wireless hub in Block S130, transmitting an identifier of the wearable device, an identifier of the action, and a fall alarm to the wireless hub in Block S140, and wirelessly disconnecting from the wireless hub in Block S150. This variation of the method S100 also includes: remotely from the wearable device, linking the fall event to the identifier of the action as an action leading to the fall event in a resident record associated with the identifier of the wearable device in Block S180; and dispatching a care provider to a location proximal the wearable device in Block S170.

Figure 3:
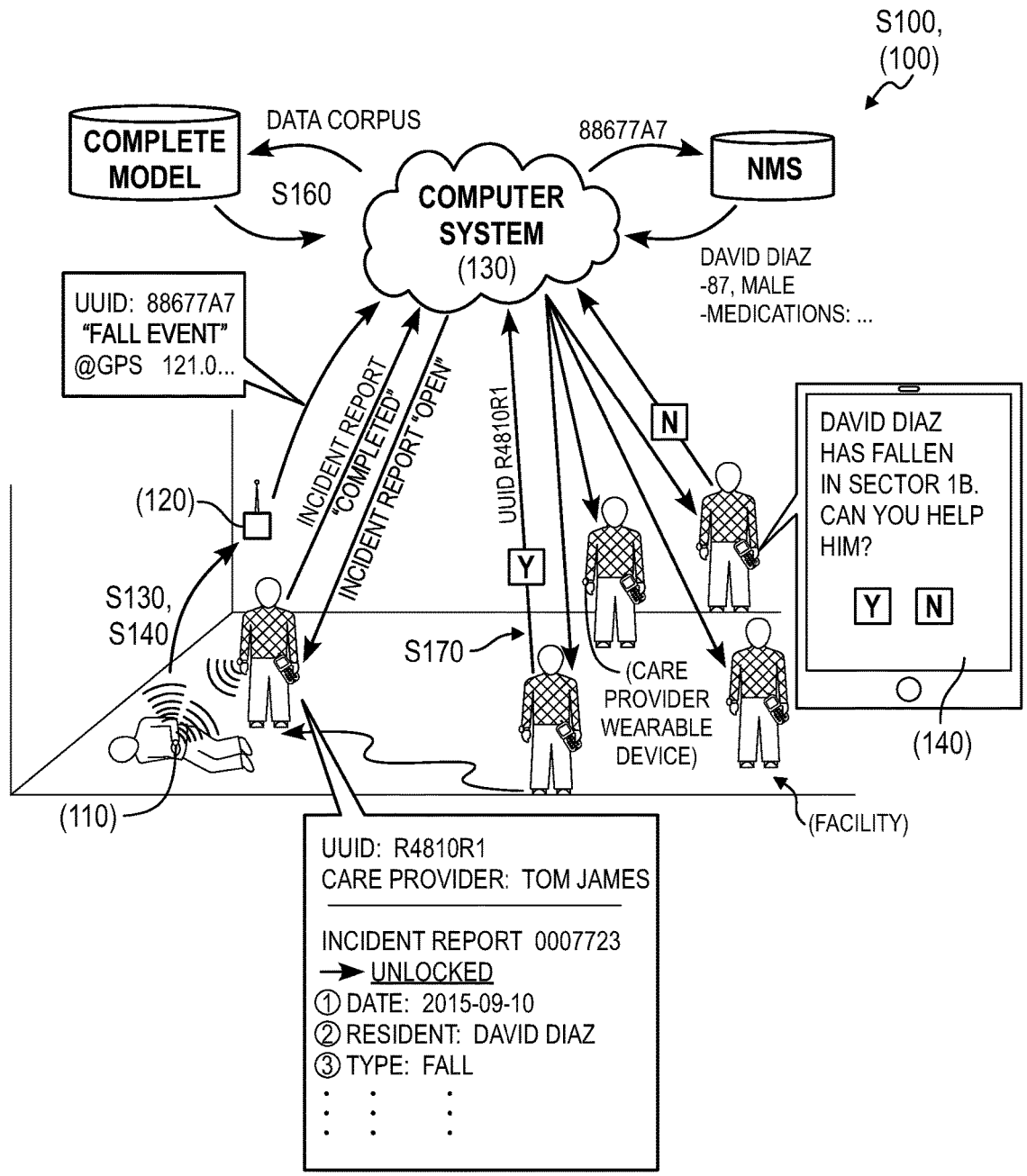
FIG. 3 is a flowchart representation of one variation of the method.

As shown in FIG. 3, the method S100 can be executed by a system including: a set of local wireless hubs 120; a wearable device 110 assigned to a resident occupying the facility and including a motion sensor and an ambient pressure sensor; and a remote computer system 130 remote from the facility. The wearable device is configured to: write motion data read from the motion sensor and ambient pressure data read from the ambient pressure sensor to a buffer; pass motion data and ambient pressure data into a compressed fall detection model stored locally to detect a fall event at a first time, the compressed fall detection model defining a compressed form of a complete fall detection model; and broadcast a corpus of sensor data from the buffer and a cue for confirmation of the fall event to a first local wireless hub in response to detecting the fall event, the first local wireless hub in the set of local wireless hubs and proximal the wearable device at the first time, the corpus of sensor data corresponding to a duration of time terminating at approximately the first time. The remote computer system is configured to: receive the corpus of sensor data from the first local wireless hub via a computer network; pass the corpus of sensor data into the complete fall detection model to confirm the fall event; and transmit a prompt to assist the resident to a computing device affiliated with a care provider within the facility in response to confirming the fall event.

2. Applications

Generally, Blocks of the method S100 can be executed by a wearable device and by a remote computer system to detect and confirm a fall by a resident wearing the wearable device. In particular, the wearable device can execute a compressed fall detection model tailored for implementation on a compact device and characterized by a low rate of false-negative fall event outputs; and the remote computer system can execute a complete fall detection model requiring greater memory than the compressed fall detection model also characterized by greater precision. The wearable device can therefore selectively and intermittently communicate with the remote computer system when a fall event is detected locally in order to prompt the remote computer system to confirm the fall event and to dispatch a care provider to the resident's location, thereby limiting power consumption by the wearable device while maintaining access to a relatively high-precision fall detection model.

By selectively returning sensor data for further fall detection analysis only after the wearable device has detected a possible fall event with a smaller-memory-footprint locally-stored fall detection model, the wearable device can function as a pre-filter of a larger-memory-footprint fall detection model executing deeper, more complex logic on a remote computer system exhibiting greater processing capabilities and memory than the wearable device. Because accuracy of the neural network (or other model) in detecting a fall event may be proportional to a size (e.g., depth, a number of nodes, a memory footprint) of the neural network, the wearable device can upload sensor data collected locally to the remote computer system for processing, which may yield (relatively) high-accuracy results. However, because uploading sensor data from the wearable device to the remote computer system (e.g., to a local wireless hub over a local wireless network) may be relatively power-intensive, the wearable device can implement a smaller—and therefore less-accurate—fall detection model to detect possible fall events and only upload sensor data to the remote computer system for processing when a possible fall event is detected, thereby extending battery life of the wearable device substantially without sacrificing accuracy of fall events by the system In one implementation, the remote computer system executes a complete fall detection model that includes a recurrent artificial neural network, and the wearable device executes a compressed fall detection model that includes a compressed form of the complete fall detection model and is of a (reduced) size suitable for execution on a wearable device. In particular, the wearable device can store and execute a compressed (i.e., reduced-size) version of the recurrent artificial neural network in order to detect fall events locally and without necessitating a wireless connection to the remote computer system; and the remote computer system—remote from a wearable device—can maintain and execute the recurrent artificial neural network for fall detection in order to confirm fall events received from the wearable device. The wearable device can thus execute Blocks of the method S100 to pass sensor data into the locally-stored compressed fall detection model to detect falls by a resident wearing the wearable device and to upload these sensor data to the remote computer system when a fall event is detected; and the remote computer system can similarly execute Blocks of the method S100 to pass these sensor data into the complete fall detection model to confirm or invalidate the fall event.

Therefore, the wearable device, a network of wireless hubs, and a remote computer system (hereinafter a "system") can execute Blocks of the method S100 to detect a fall event locally at a wearable device and substantially in real-time and to then confirm the fall event remotely from the wearable device where greater computing power is available by processing sensor data collected by the wearable device with a more comprehensive fall detection model in order to reduce false positive fall events. In particular, rather than continuously uploading sensor data to the remote computer system for processing, the wearable device can intermittently upload bursts of data to the remote computer system, such as once per three-minute interval, throughout regular operation. The wearable device can also upload fall alarms with corresponding sensor data to the remote computer system only when a fall event is detected locally at the wearable device in order to reduce power consumption at the wearable device due to wireless communication substantially without sacrificing precision (i.e., accuracy and repeatability) of fall detection by the system.

Blocks of the method S100 can therefore be executed by a computer system, such as on a local computer system within an assisted living facility (e.g., a local server), by a remote computer system in the cloud, or by a distributed computer network, etc. (hereinafter "remote computer system"). In particular, the remote computer system can interface with multiple devices within and around a facility in order to detect, confirm, and respond to fall events by residents within the facility. Furthermore, the method S100 is described herein as implemented within or in conjunction with an assisted living facility. However, the method S100 can be similarly implemented within a general hospital, a psychiatric hospital, a preschool, a summer camp, or any other health institution, clinic, or community, etc.

3. Fall Detection Models

As described above, the system can maintain and execute a complete fall detection model including an artificial neural network (e.g., a recurrent artificial neural network with Gated Recurrent Units (GRU) or Long Short Term Memory (LSTM) layers) defining a set of connections, neurons, and layers through which a sensor packet from a wearable device can be passed to output a determination of presence or absence of a fall event at the wearable device, as shown in FIG. 4. (A data packet described herein can include one or more sensor output values from a single sampling period or a sequence or pattern of sensor output values collected at the wearable device over multiple sampling periods.) In particular, the remote computer system can support a greater memory footprint than the wearable device, such as by accessing multiple servers within a computer network, and can therefore apply sensor data received from a wearable device to a relatively large and substantially comprehensive fall detection model in order to detect a fall event at the wearable device with a relatively high degree of precision (e.g., repeatedly with few false positive and false negative fall events).

However, because the wearable device is configured to be worn by a resident (e.g., on the resident's wrist) or integrated into clothing worn by the resident, the wearable device may exhibit more limited size constraints than the remote computer system and may therefore feature less physical space to house memory capable of supporting the memory footprint of the complete fall detection model. The wearable device can therefore store and execute a compressed fall detection model that filters sensor data, detects substantially all true positive fall events, and detects some false positive fall events, as shown in FIG. 4. By implementing the compressed fall detection model, the wearable device can selectively and intermittently upload sensor data to the remote computer system for further processing when a fall detection event is detected by the wearable device. The remote computer system can then execute the complete fall detection model to reprocess these sensor data to confirm or reject the fall event.

Therefore, while the compressed fall detection model may exhibit a higher frequency of false positive fall events than the complete fall detection model, the wearable device and the remote computer system—executing the compressed and complete fall detection models, respectively—can cooperate to confirm a fall event by a resident wearing the wearable device with a high degree of precision and in (near) real-time despite limited size of the wearable device and despite intermittent communication between the wearable device and the remote computer system.

3.1 Compressed Fall Detection Model Generation

In one implementation, the remote computer system generates the compressed fall detection model from a subset of prioritized neurons and connections in the complete fall detection model. Alternatively, the remote computer system can create and train a compressed fall detection module that is inherently "smaller" than the complete fall detection module. In particular, the remote computer system can assemble a smaller fall detection model that requires a maximum memory footprint that falls within memory limits of a wearable device by removing lower-priority (e.g., lower-weight) connections and/or neurons from the complete fall detection model. For example, the compressed fall detection model can include a first recurrent neural network defining a first quantity of nodes that outputs a confidence score for occurrence of a fall event at the wearable device (i.e., by a resident wearing the wearable device). In this example, the complete fall detection model can include a second recurrent neural network defining a second quantity of nodes—greater than the first quantity of nodes in the first recurrent neural network—that similarly outputs a confidence score for occurrence of the fall event at the wearable device.

The complete and compressed fall detection models can also contain different weights between like neurons in their corresponding artificial neural networks in order to achieve different sensitivities to possible fall events. In particular, the compressed fall detection model can contain a set of connection weights that yields a lower overall threshold for detecting a fall event from a set of sensor data (e.g., a data packet) recorded at the wearable device; and the complete fall detection model can contain a set of connection weights that yield a higher overall threshold for detecting a fall event from the same set of sensor data received from the wearable device. In this implementation, the remote computer system can tune weights of connections between neurons in the compressed neural network to achieve a reduced threshold—or increased sensitivity—to falls compared to the complete neural network. Alternatively, the system can selectively incorporate neurons, connections, and/or layers from the complete neural network into the compressed neural network in order to achieve a target threshold for detecting a fall event that is less than a threshold for detecting a fall event with the complete neural network for like sensor data. Therefore, though the system can maintain and update a complete fall detection model and a compressed fall detection model from the same set of sensor data collected from one or more deployed wearable devices, the complete and compressed fall detection models can exhibit different, tailored sensitivities to fall events in order to limit instances of communication between the wearable device and the remote computer system while maintaining a substantially low frequency of false positive and false negative fall events. In particular, when executing the compressed fall detection model, the wearable device can detect fall events with a relatively high rate of false positives (but low rate of false negatives) in Block S120; however, in response to detection of a fall event, the wearable device can upload a fall alarm and sensor data that triggered the fall alarm to the remote computer system in Block S150, and the remote computer system can apply these sensor data to the complete fall detection model to reject false positive fall events in Block S160.

The system is described herein as including a remote computer system that maintains and executes a complete fall detection model and a wearable device that executes a compressed fall detection model. However, the remote computer system and the wearable device can execute fall detection models of the same size (i.e., requiring the same memory footprint) but with different weights, as described above. Yet alternatively, the remote computer system can maintain (i.e., update based on labeled data collected from deployed wearable devices) a fall detection model over time, as described below, and the wearable device can execute the fall detection model locally to the exclusion of the remote computer system. Furthermore, the remote computer system can include one or more local or distributed computer systems that collectively or separately train the complete fall detection model and detect fall events with data received from the wearable device.

3.2 Intermediate Fall Detection Model

In one variation described below and shown in FIG. 4, a local wireless hub executes an intermediate fall detection model representing a compressed (or "abbreviated") version of the complete fall detection model. Generally, a local wireless hub can define an intransient interface between wearable devices nearby and the remote computer system, can define a larger physical footprint than the wearable device, and can be plugged into an electrical outlet in the facility to access more, substantially uninterrupted power. Therefore, the local wireless hub can include a processor exhibiting more processing power and memory than the wearable device but less than the remote computer system. Thus, the local wireless hub can execute an intermediate fall detection model that defines a memory footprint smaller than that of the complete fall detection model and larger than that of the compressed fall detection model.

For example, upon receipt of contents of a buffer and a cue to retest these sensor data from a wearable device, the local wireless hub can pass these sensor data into a local instance of the intermediate fall detection model to reconfirm a fall event detected by the wearable device before transmitting these buffer contents and a cue to retest these sensor data to the remote computer system. In particular, the local wireless hub can implement the intermediate fall detection model to confirm a fall event to a greater degree of confidence or with a greater degree of accuracy before releasing resident data to the remote computer system outside of the facility. In another example, the local wireless hub: automatically attempts to connect with the remote computer system upon receipt of contents of a buffer and a cue to retest these sensor data from a wearable device; returns these sensor data and the cue to the remote computer system when a connection to the remote computer system (e.g., via a cellular network, the Internet, and local area network, etc.) is established; and passes these sensor data through the intermediate fall detection model to confirm the fall event with a greater degree of confidence locally and triggers local dissemination of prompts to assist the resident only if the local wireless hub fails to establish a connection to the remote computer system (e.g., within a threshold time of five seconds).

In this variation, the remote computer system can implement methods and techniques described above to generate and refine the intermediate fall detection model. For example, the compressed, intermediate, and complete fall detection models can be configured to yield very small rates (e.g., <1%) of false negative fall events. However, the compressed fall detection model can be configured to yield a higher false positive rate (e.g., 8%) than the intermediate fall detection model; and the intermediate fall detection model can be configured to yield a higher false positive rate (e.g., 4%) than the complete fall detection model (e.g., <1%). Therefore, the wearable device, the set of local wireless hubs, and the remote computer system can cooperate to detect substantially all true positive fall events while rejecting false positive fall events with greater accuracy as greater resources (e.g., computing power, network bandwidth) are allocated to distribute and process sensor data collected by the wearable device.

4. System

As shown in FIG. 3, the system executing Blocks of the method S100 can include: a set of local wireless hubs distributed throughout a facility, a set of wearable devices assigned to residents of the facility; a set of computing devices assigned to the group of care providers; and a remote computer system that accesses data from these wearable devices via the set of local wireless hubs and a computer network (e.g., the Internet) in order to monitor residents, detect fall events within the facility, and to prompt care providers to respond to fall events substantially in real-time via their assigned computing devices.

4.1 Resident Wearable Device

Generally, a wearable device 110: is assigned to a resident; includes a set of sensors; writes sensor data read from the set of sensors to a buffer (e.g., a circular or rolling) of limited duration; regularly passes sensor data into a compressed (e.g., smaller-memory-footprint) fall detection model to detect possible fall events; and selectively uploads sensor data to the remote computer system via a local wireless hub when a fall event is detected by the compressed fall detection module (e.g., to at least a threshold confidence) for confirmation of the fall event by the remote computer system, which executes a complete (e.g., larger-memory footprint) fall detection module exhibiting greater precision in detecting fall events, as shown in FIG. 4.

Figure 2:
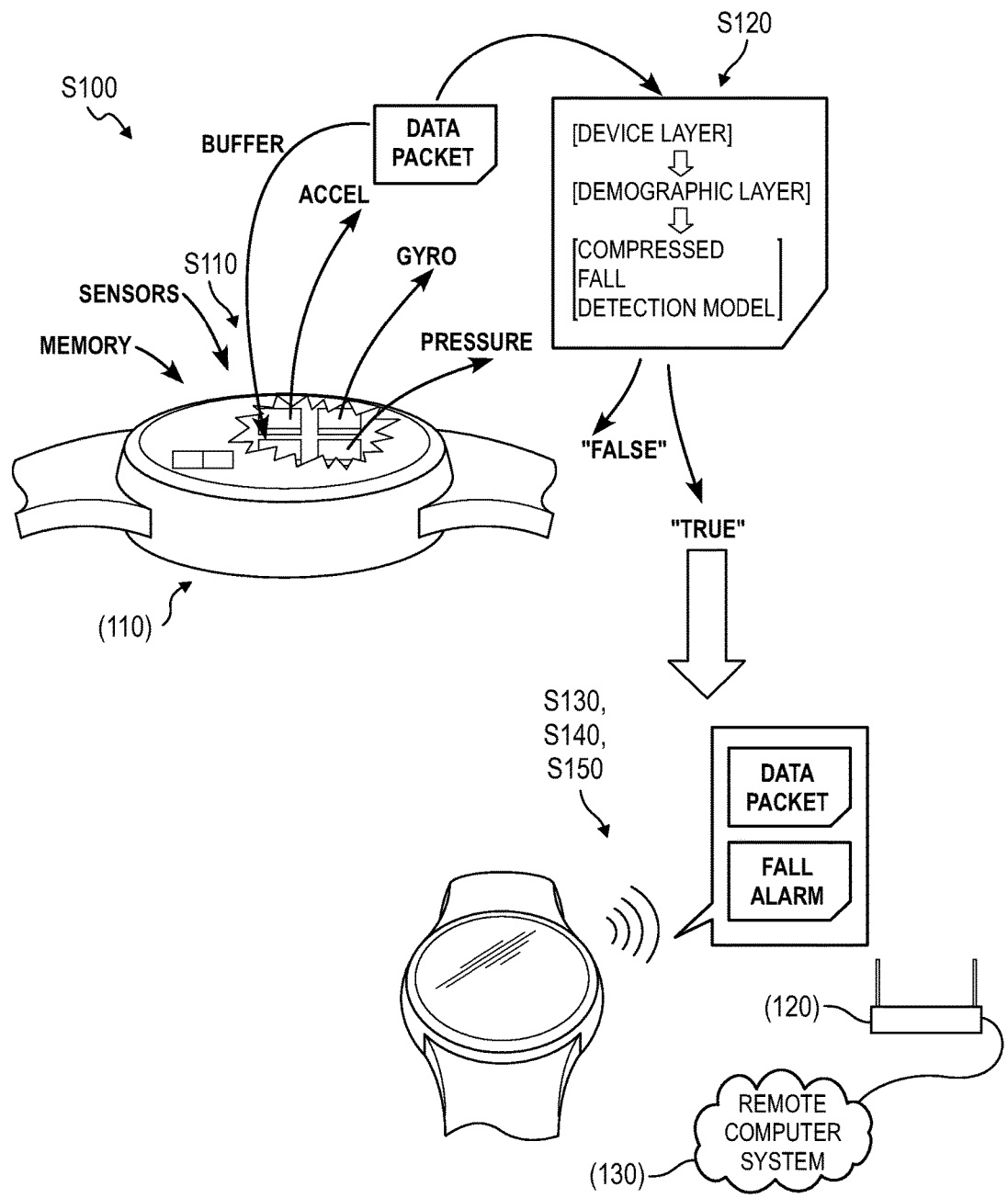
FIG. 2 is a flowchart representation of one variation of the method.

The wearable device 110: is configured to be worn by a resident; contains internal sensors; and functions to sample the internal sensors throughout operation, writes sensor data from the internal sensors into a buffer in Block S110, and detects a fall event by passing sensor data into a compressed fall detection model stored locally on the wearable device 110 in Block S120, as shown in FIG. 2. Furthermore, in response to detection of the fall event, the wearable device 110 wirelessly connects to a local wireless hub in Block S130, transmits sensor data from the buffer and a cue for fall event confirmation to the wireless hub in Block S140, and wirelessly disconnects from the wireless hub in Block S150 once these data are uploaded to the wireless hub. Generally, the wearable device 110 functions to detect fall events (i.e., instances in which a resident wearing the wearable device 110 falls) and to distribute fall event data to the remote computer system substantially in real-time to enable rapid (e.g., near-real-time) dispatch of a care provider to the fallen resident.

In one implementation, an administrator of the assisted living facility (hereinafter "facility") can access an administrator interface to assign a resident of the facility one or more (i.e., a set of) wearable device 110s. In one example, the administrator assigns a wearable device 110 to each resident; each resident wears her assigned wearable device 110 continuously over a period of time (e.g., one week) before recharging the wearable device 110, thereby enabling the wearable device 110 and the remote computer system to continuously monitor the resident for possible fall events. Each wearable device 110 can be loaded with a unique ID (e.g., a UUID), and the unique ID can be associated with a particular resident of the facility, such as in a name mapping server (or "NMS"), as shown in FIGS. 1 and 2.

The wearable device 110 can include: a (three-axis) gyroscope; an (three-axis) accelerometer; a compass; a barometer; a skin temperature sensor; a heart rate sensor; and/or one or more other internal sensors, as shown in FIG. 2. The wearable device 110 can also include: a processor configured to pass data from one or more of these sensors into the compressed fall detection model in order to detect a fall event; a memory module that stores sensor data (e.g., data packets) in a buffer of limited duration (e.g., one minute, three minutes); a rechargeable battery that powers the foregoing elements; and/or a wireless communication module that broadcasts fall event data to local wireless hubs when the processor detects a fall event and that broadcasts beacons to local wireless hubs throughout the facility to enable the remote computer system to track the location of the wearable device 110—and therefore the resident—throughout the facility over time. The processor can sample the set of internal sensors at a single static sampling rate or at different and/or dynamic sampling rates. For example, the processor can sample the gyroscope and accelerometer at a sampling rate of 100 Hz, sample the heart rate sensor once per minute ($\frac{1}{60}$ Hz), and sample the skin temperature sensor once per three-minute interval ($\frac{1}{300}$ Hz).

4.2 Care Provider Computing Device

A computing device is worn or carried by a care provider and functions to audibly and/or visually serve fall event prompts—received from the remote computer system—to the care provider, collects incident report data responsive to a fall event from the care provider, and interfaces with hubs throughout the facility to track the location of the care provider over time, such as to enable the remote computer system to selectively target fall event prompts to care providers in the facility nearest a resident in need of assistance.

As described above, the administrator of the assisted living facility can assign or otherwise equip a care provider—employed by the facility—with a computing device. For example, each computing device can be assigned and can store in local memory a unique ID (e.g., a UUID), and each computing device ID can be associated with a particular care provider at the facility, such as in a NMS.

In one implementation, a computing device includes a touchscreen and a wireless communication module and executes a care provider application 140, such as within a web browser or as a native application. For example, the care provider application 140 can: receive a fall event prompt from a local or remote computer system via the wireless communication module; alert a care provider of the fall event prompt and receive a response to the fall event prompt (e.g., "Yes, I will respond" or "No, I cannot respond right now") from the care provider through the integrated touchscreen; upload the care provider's response to the fall event prompt to the remote computer system via the wireless communication module; serve an incident report to the care provider through the touchscreen upon receipt from the remote computer system; populate the incident report with data entered manually by the care provider through the touchscreen; and communicate the complete incident report back to the remote computer system via the wireless communication module. The wireless communication module in the computing device can also broadcast beacons to local wireless hubs throughout the facility to enable the remote computer system to track the location of the computing device—and therefore the care provider—throughout the facility over time. Furthermore, the care provider application 140 executing on the computing device can implement "proximity card" methods to confirm that the care provider equipped with the computing device has made contact with a resident based on outputs of an inertial sensor or proximity sensor, such as when the care provider taps his computing device against a wearable device worn by a resident while responding to a fall event.

In the foregoing implementation, the computing device can define a smart watch. Alternatively, the computing device can define a tablet, smartphone, or other mobile computing device. However, the computing device can be of any other type of form.

4.3 Wireless Hub

The wireless hub 120 functions to bridge communications between the wearable device and the remote computer system. In one implementation, the wireless hub 120 supports a first wireless communication protocol enabled at the wearable device, supports a second wireless communication protocol enabled at a local Internet-connected wireless router or cellular tower, and routes data between the first and second wireless communication protocols in order to communicate data between the wearable device and the remote computer system.

In the variation described above in which the local wireless hub 120 is loaded with an intermediate fall detection model, the local wireless hub 120 can also include: local memory configured to store the intermediate fall detection model; and a processor configured to pass a corpus of sensor data received from the wearable device into the intermediate fall detection model to detect or confirm a fall event, such as by calculating a confidence score for occurrence of a fall event during a period of time represented by the corpus of sensor data.

4.4 Remote Computer System

In one variation, the remote computer system 130 includes a remote server located remotely from the facility and configured to communicate with local wireless hubs throughout the facility via a cellular network or computer network (e.g., the Internet). Alternatively, the remote computer system 130 can include a local server or other computer system 130 arranged within the facility and configured to communicate with the local wireless hubs throughout the facility via a local area or wireless network. However, the remote computer system 130 can include any other type of computer system 130 arranged within or outside of the facility.

5.1 Data Collection

Block S110 of the method S100 recites, at the wearable device, writing sensor data from a sensor integrated into the wearable device to a buffer. Generally, in Block S110, the wearable device regularly samples various internal sensors—such as a three-axis accelerometer, a three-axis gyroscope, a skin temperature sensor, and/or an ambient pressure sensor, as described above—and writes these sensor data to a buffer (e.g., a circular buffer) of fixed length (e.g., representing a fixed buffer duration of three minutes).

In one implementation, the wearable device selectively samples its sensors throughout operation, such as to reduce power and/or memory consumption. In one example, when powered ON and throughout operation, the wearable device samples the skin temperature sensor once per minute. In this example, if an output of the skin temperature sensor drops below a threshold temperature value (e.g., 94° F.) associated with separation of the wearable device from a resident (e.g., removal from the resident's wrist), the wearable device can deactivate all other sensors. However, once output of the skin temperature sensor exceeds the threshold temperature value, the wearable device can activate the accelerometer and heart rate sensor, such as by sampling the accelerometer at 100 Hz and sampling the heart rate sensor once per three-minute interval (i.e., a rate of $\frac{1}{300}$ Hz) in addition to sampling the temperature sensor at a rate of once per minute (i.e., a rate of $\frac{1}{60}$ Hz). Following a magnitude of an acceleration vector—generated from three axial acceleration values output by the accelerometer—that exceeds a threshold acceleration value, the wearable device can sample the gyroscope and the barometer, such as at a rate of 100 Hz, for a period of ten seconds following a last acceleration magnitude exceeding this threshold acceleration value.

In the foregoing example, if the resident is also wearing a glucose monitor, the wearable device can intermittently wirelessly connect to and download glucose level data from the glucose monitor. In this example, the wearable device can attempt to wirelessly connect to and download glucose data from the glucose monitor, such as once per eight-minute interval ($\frac{1}{480}$ Hz), regardless of an output of the skin temperature sensor in the wearable device. Therefore, if the resident is sleeping or resting with her assigned wearable device on a table nearby—rather than wearing the wearable device while sleeping or resting—the wearable device can continue to collect glucose data from the glucose monitor while other sensors (e.g., the accelerometer, gyroscope, and heart rate sensor) in the wearable device are inactive due to a low temperature detected by the skin temperature sensor while the wearable device is not worn.

5.2 Buffer

Throughout operation, the wearable device can write these sensor data to corresponding sensor streams in a buffer stored in local memory on the wearable device, as shown in FIGS. 1 and 4. In one implementation, the wearable device stores data read from these sensors in discrete timestamped data packets throughout operation. For example, a single data packet can include placeholders for three acceleration values, three gyroscope values, one skin temperature value, one heart rate value, one glucose level value, and one time/data value (i.e., a timestamp), etc., and the wearable device can populate the single data packet with sensor values collected during a sampling period corresponding to the timestamp written to the data packet. However, because the wearable device may sample various internal (and external) sensors at different rates, the wearable device can generate a data packet that does not contain values read from all of these sensors. Throughout operation, the wearable device can store these data packets in local memory, such as by writing these data packets to a buffer. For example, the buffer can be configured to store a limited number of data packets (e.g., 30,000 data packets), a set of data packets collected over a limited duration of time (e.g., three minutes), or a set of data packets of a limited size (e.g., 100 kilobytes) and collected over a contiguous period of time, etc. Upon recording a new data packet following a sampling period, the wearable device can store the new data packet in the buffer and delete an oldest data packet from the buffer. The wearable device can also pass each new data packet (or sequences of data packets) through a compressed fall detection model executing locally on the computing device to detect a possible fall event substantially in real-time, as described below.

6. Data Offloading and Local Fall Detection

Block S120 of the method S100 recites, at the wearable device, inputting sensor data read from the sensor into a compressed fall detection model stored locally on the wearable device to detect a fall event at a first time, wherein the compressed fall detection model defines a compressed form of a complete fall detection model. Generally, in Block S120, the wearable device implements the compressed fall detection model to locally predict a recent or concurrent fall event based on sensor data collected during and/or immediately preceding the current sampling period.

Blocks S130, S140, and S150 recite, respectively, at the wearable device: wirelessly connecting to a local wireless hub; transmitting a corpus of sensor data from the buffer and a cue for confirmation of the fall event to the wireless hub, wherein the corpus of sensor data corresponds to a duration of time terminating at approximately the first time; and wirelessly disconnecting from the wireless hub. Generally, in Blocks S130, S140, and S150, the wearable device selectively wirelessly connects to a local wireless hub, offloads contents of its buffer to the local wireless hub for distribution to the remote computer system, and then wirelessly disconnects from the local wireless hub in order to limit power consumption by the wearable device.

Throughout operation, the wearable device can regularly broadcast a wireless beacon to trigger a local wireless hub near the wearable device to wirelessly connect (or "pair") with the wearable device for transfer of contents of the buffer to the remote computer system for storage in Block S130. For example, the wearable device can broadcast a wireless beacon when the buffer is 95% full, when a buffer timer (e.g., a three-minute timer) expires, or when a threshold number of data packets (e.g., 30,000 data packets) have been recorded to the buffer, etc. Once paired with the wireless hub, the wearable device can upload the full contents of the buffer and an ID (e.g., a UUID) of the wearable device to the wireless hub in Block S140, and the wireless hub can pass these data packets and wearable device ID to the remote computer system. Once the wearable device has uploaded these data to the wireless hub, the wearable device can disconnect from the wireless hub in order to limit power consumption in Block S150. The remote computer system can also store these sensor data received from the wearable device—via the local wireless hub—in a remote database for asynchronous processing, such as: to train the complete fall detection model on data correlated with non-fall events; or to extract motion and ambient pressure data indicative of a fall event not detected by the compressed fall detection model executed on the wearable device following indication of a fall event by a corresponding resident or by a care provider at the facility and to retrain the complete and compressed fall detection models accordingly.

However, if the wearable device detects a fall event in the midst of a buffer cycle, the wearable device can interrupt transfer of sensor data from the buffer to the remote computer system in order to upload contents of the buffer and a cue (i.e., a trigger, a prompt, a flag)—to retest these data for a fall event with the complete fall detection model—to the remote computer system via a local wireless hub substantially in real-time as the wearable device detects a fall event. In particular, as the wearable device generates each subsequent data packet, the wearable device can pass a new data packet into the compressed fall detection model to determine if the resident was falling during the current and/or immediately-preceding sampling periods. For example, the wearable device can calculate a confidence score for occurrence of a fall event at the wearable device based on: a low-frequency change in ambient pressure values read from an ambient pressure sensor integrated into the wearable device over a period of time (e.g., a change in barometric pressure indicating a change in altitude greater than one half of one meter within one second); and similarity of motion data—read from an accelerometer and a gyroscope integrated into the wearable device over this period of time—to a motion pattern of a fall represented in the compressed fall detection model, such as for a known location of the wearable device on the resident (e.g., one of the resident's wrists).

The wearable device can then execute a fall response routine if: the output of the compressed fall detection model indicates that the resident was falling during the current or immediately-preceding sampling period; a threshold number of sequential outputs of the compressed fall detection model indicate that the resident was falling during a corresponding contiguous sequence of sampling periods; or outputs of the compressed fall detection model indicate that the resident was falling during a threshold proportion of a sampling periods with a corresponding sequence of sampling periods, such as with a confidence score greater than the threshold confidence value. During a fall response routine, the wearable device can: connect to a local wireless hub in Block S130; upload a corpus of sensor data from the buffer (e.g., the full contents of the buffer or a limited number of data packets that triggered the fall response routine), a cue to confirm the fall event, and an ID of the wearable device to the wireless hub in Block S140; and then disconnect from the wireless hub in Block S150. In particular, the wearable device can upload the complete contents of its buffer to the local wireless hub, such as including a single data packet or a set of data packets that triggered detection of the fall event, labeled as data packets of interest. Alternatively, the wearable device can upload only a limited subset of data packets from the buffer to the local wireless hub, such as including a set of data packets that triggered detection of the fall event and a limited sequence of data packets (e.g., spanning a duration of five seconds) preceding the detection of the fall event. The remote computer system can then process data packets related to initial detection of the fall event to confirm or reject the fall event in Block S160.

Once the wearable device uploads contents of the buffer and the cue to a local wireless hub nearby, the wearable device can return to: recording data packets to the buffer in Block S110; intermittently connecting to a local wireless hub on regular intervals in Block S130; and uploading contents of the buffer to the remote computer system via the wireless hub in Block S140, a described above.

Alternatively, the wearable device can maintain two buffers of different lengths and can write sensor data to these two buffers over time. For example, the wearable device can maintain a short-term buffer of first duration (e.g., thirty seconds, three minutes) and a long-term buffer of a second duration greater than the first duration (e.g., 24 hours). As the wearable device reads new sensor values from its internal sensors, the wearable device can: run these new sensor data through the compressed fall detection model, as described above to check for a fall event; write these new sensor values to the short-term buffer; and shift oldest sensor values from the short-term buffer to the long-term buffer. If the compressed fall detection model detects a fall event, the wearable device can push the contents of the buffer (or a subset of sensor values in the buffer that triggered detection of the fall event) to a local wireless hub for distribution back to the remote computer system in Block S140. At the conclusion of the duration of the long-term buffer (e.g., once per day), the wearable device can offload the contents of the long-term buffer to the remote computer system for storage and/or further processing, as described below.

7. Resident Location

Throughout operation, the wearable device can regularly broadcast a location beacon, such as at a rate of 3 Hz while also filling a buffer defining a length of three minutes and regularly uploading contents of the buffer to the remote computer system via local wireless hubs on three-minute intervals. Local wireless hubs within wireless range of the wearable device throughout the facility can receive these location beacons and return various related data to the remote computer system, such as: a UUID of the wearable device; a UUID of the local wireless hub that received the beacon; a signal strength of the location beacon upon receipt from the wearable device; and/or a time at which the location beacon was received. The remote computer system can aggregate these data received from multiple local wireless hubs into an approximate location of the wearable device based on known locations of these local wireless hubs. For example, the remote computer system can implement RSSI techniques to compile signal strength and receipt times of the location beacon received by one or more local wireless hubs to estimate the location of the wearable device at the corresponding instant in time. The remote computer system can repeat this process over time (e.g., at a rate of 3 Hz) to track the location of the wearable device—and therefore the location of the associated resident. When a fall event is detected by the wearable device and subsequently confirmed by the remote computer system, the remote computer system can thus dispatch a care provider to the location of the wearable device to assist the resident, as described below.

8. Fall Event Handling

As described above, once the remote computer system receives a fall alarm, a corpus of sensor data, and a device ID from a wearable device, the remote computer system can pass the corpus of sensor data into the complete fall detection model to confirm the fall event in Block S160.

In one implementation, if the complete fall detection model—loaded with the corpus of sensor data—outputs a value that indicates that the fall event detected by the wearable device (likely) constitutes a false positive, the remote computer system can return a prompt to the wearable device—via a computer network and local wireless hubs in the facility—to clear a fall alarm for the detected fall event. However, if the complete fall detection model—loaded with the corpus of sensor data—outputs a value indicating that the fall event detected by the wearable device (likely) constitutes a true positive, the remote computer system can initiate a fall event handling routine, such as described below. For example, the remote computer system can discard the fall event detected by the wearable device if the complete fall detection model outputs a confidence score—for occurrence of a fall event involving the wearable device—that remains below a global threshold score; similarly, the remote computer system can execute a fall event handling routine if the complete fall detection model outputs a confidence score that exceeds the global threshold score, as described below.

During a fall event handling routine, the remote computer system can: identify the location of the wearable device based on known locations of local wireless hubs that recently received location beacons from the wearable device, as described above; identify the resident assigned to the wearable device; then dispatch a care provider to the location of the wearable device, as shown in FIGS. 1 and 3, to assist. For example, upon confirmation of the fall event, the remote computer system can pass the UUID of the wearable device into a name mapping system to retrieve a resident ID—such as including a name, a health status, a current health condition, and/or a most-current photographic image, etc. of the resident—assigned to the wearable device.

The remote computer system can then: aggregate these data into a fall response prompt indicating that a resident has fallen, specifying a last known location of the resident, and indicating various resident data (e.g., the resident's name, age, gender, known medical complications, etc.); and distribute this fall response prompt to care providers in the facility in Block S110, as described in U.S. patent application Ser. No. 15/339,771. For example, care provider computing devices issued to care providers throughout the facility can regularly broadcast location beacons readable by local wireless hubs arranged at known locations throughout the facility, and the remote computer system can implement methods and techniques described above to track locations of care providers throughout the facility based on known locations of local wireless hubs that received these location beacons from these care provider computing devices. In this example, the remote computer system can selectively transmit the fall response prompt: to a single care provider computing device nearest the last recorded location of the resident's wearable device; to a set of care provider wearable devices within a threshold distance (e.g., within 100 feet) of the last recorded location of the resident's wearable device; or to a set of care provider wearable devices occupying the same room, the same floor, the same building, or the same outdoor space as the resident's wearable device.

In the foregoing implementation, the remote computer system can distribute a fall response prompt to a care provider in the facility in the form of a text message, a push notification within a native application or web browser executing on the care provider's computing device, or in any other format, as shown in FIG. 3. The fall response prompt can also include a prompt to confirm or discard the fall response prompt. For example, if a first care provider to receive the fall response prompt discards the fall response prompt via her assigned computing device, the remote computer system can serve the fall response prompt to a computing device of a next care provider and repeat this process until a care provider confirms through her assigned computing device that she will assist the resident. Once a care provider confirms that she will respond to the fall event, once a calculated location of the care provider's computing device falls within a threshold distance of the last known location of the resident's wearable device, or once a wireless connection or physical contact between the care provider's computing device and the resident's wearable device indicate that the care provider is present at the resident's location, the remote computer system can serve an incident report to the care provider's computing device or enable access to the incident report through a care provider portal affiliated with the care provider. For example, the remote computer system can automatically populate the incident report with: resident information (e.g., name, age, gender, etc.); responding care provider information (e.g., name, employee ID); duration of time from detection of the fall event to arrival of the responding care provider to the resident's location; a type of the incident (e.g., a fall); etc. The remote computer system can also: interpret a magnitude of the fall event from sensor data received from the resident's wearable device, such as based on a rate of change in altitude of the wearable device during the fall event and/or by extracting a magnitude of the resident's impact with the ground based on acceleration values recorded by the wearable device during the fall event; and automatically write this magnitude of the fall event to the incident report.

Therefore, upon dispatching a care provider to assist the resident, the remote computer system can: access a digital incident report; insert a name of the resident, affiliated with the wearable device, into the digital incident report; insert a prompt to verify the fall event into the digital incident report; and transmit the digital incident report to a computing device affiliated with the care provider. The care provider can then manually complete remaining elements in the incident report during or after assisting the resident. For example, the care provider can manually enter confirmation that the resident was involved in a fall event, an apparent magnitude of the fall event, apparent injuries sustained by the resident during the fall event, etc. into the incident report through her computing device. The remote computer system can then: automatically label the corpus of sensor data—received from the wearable device responsive to the detected fall event—with confirmation or rejection of the fall event entered into the incident report by the care provider; and retrain the compressed and complete (and intermediate) fall detection models based on these new labeled data.

9. Fall Event Triggers

As described above, the wearable device can regularly pass sensor data into the compressed fall detection model to detect a fall event with a first degree of certainty in Block S120 and can upload sensor data from the buffer to the remote computer system in Block S140 when a fall event is detected; the remote computer system can then pass these sensor data into the complete fall detection model to confirm or reject the fall event with a greater degree of certainty.

9.1 Static Confidence Scores

In one implementation, the wearable device implements a local threshold score—to trigger dissemination of sensor data to the remote computer system for further testing—that enables a limited false negative rate (e.g., <1%) at the expense of a higher false positive rate for detected fall events. In this implementation, the remote computer system implements a global threshold score—to trigger dissemination of fall response prompts to care providers in the facility—tailored to the deeper, more complex complete fall detection model in order to maintain this limited false negative rate while also reducing the expense of a higher false positive rate for detected fall events.

For example, the compressed fall detection model can output a first confidence score for a possible fall event; if the first confidence score exceeds a local threshold score, the wearable device can upload these data packets and a cue to retest these data packets to the remote computer system. Upon receipt, the remote computer system can pass these data packets into the complete fall detection model to calculate a second confidence score and confirm the fall event if the second confidence score exceeds a global threshold score. In this example, to maintain a low false negative rate with a fall detection model of limited memory footprint size, the local confidence score implemented by the wearable device to detect a fall event can be set relatively low (e.g., 80%), which may also yield a relatively high false positive rate for fall events detected by the wearable device. However, to reject these false positives, the remote computer system can implement a deeper, more complex fall detection model and a global threshold score (e.g., 90%) that is greater than the local threshold score implemented by the wearable device.

9.2 Dynamic Confidence Scores

In another implementation, the wearable device dynamically adjusts a confidence score for detecting a fall event based on biometric data read from biometric sensors integrated into the wearable device. In one example, the wearable device: includes a skin temperature sensor; and stores a confidence score model that outputs a confidence score—for detecting a fall event through the compressed fall detection model—inversely proportional to deviation of the resident's skin temperature from a target skin temperature (e.g., 98° F.). In this example, the wearable device thus: regularly samples the skin temperature sensor for a skin temperature of the resident throughout operation; calculates deviation of the resident's skin temperature from a target skin temperature; and passes one or a sequence of recent skin temperature deviations of the resident into a confidence score model to calculate a local threshold score for detecting a fall event. In particular, deviation from a target skin temperature may indicate that the resident is unwell (e.g., hypothermic if below the target temperature; feverish if above the target temperature), which may be correlated with reduced mobility of the resident and increased risk of the patient falling. Thus, the wearable device can automatically increase sensitivity to a fall event by decreasing a local threshold score for detecting a fall event as a function of (e.g., proportional to) an absolute difference between the resident's skin temperature and a generic or assigned target skin temperature.

The wearable device can also write skin temperature data to the buffer and intermittently upload these skin temperature data to the remote computer system via a local wireless hub in Block S140 when a fall event is detected; and the remote computer system can implement similar methods and techniques to adjust a global confidence score for confirming a fall event based on the resident's skin temperature, deviation from a target skin temperature, or skin temperature trend (i.e., change in skin temperature over time), etc.

In a similar implementation, the wearable device can: track the resident's mobility over time; and adjust the local threshold score based on the resident's mobility. In particular, the resident's mobility can be inversely correlated with risk of falling, and the wearable device can therefore adjust sensitivity of the compressed fall detection model to a fall event by reducing the local threshold score as a function of decreasing mobility of the resident. For example, the wearable device can convert acceleration and/or gyroscope signals into a step count of the resident over time and then reduce the local threshold score proportional to a difference between the actual step count of the resident and an average step count of the resident by the same time of day on previous days (or an average step count of a population of people of similar ages by the same time of day). In another example, the wearable device can estimate a gait length of the resident from motion data collected by sensors in the wearable device and then set the local threshold score proportional to the resident's gait length, since a longer gait may indicate greater mobility, and vice versa. (In this example, the wearable device can interface with local wireless hubs to track a total distance traveled by the resident over a period of time and divide this distance by a step count for the same period to estimate the resident's gait length.)

The remote computer system can implement similar methods and techniques to extract resident mobility from sensor data received from the wearable device and to adjust the global threshold score accordingly, thereby aligning sensitivity of the complete fall detection model for confirming a fall event to the resident's current mobility.

In yet another implementation, the remote computer system: aggregates a set of fall events occurring at the facility (or across multiple facilities) over time; and then generates a threshold score model that outputs a global threshold score as a function of time of day and/or day of week based on times and/or days on which these past fall events occurred. For example, the remote computer system can increase sensitivity of the complete fall detection model to fall events proportional to a frequency with which past fall events occurred at the same time of day, within the same time window, and/or on the same day of the week across a resident population within the facility or across multiple facilities. Therefore, in this example, the remote computer system can: calculate a frequency of historical fall events, stored in a fall event database, across a group of residents as a function of time of day; and then set the global threshold score as an inverse function of frequency of historical fall events at a current time of day.

The remote computer system can also push the same or similar threshold score model to the wearable device, and the wearable device can implement similar methods and techniques to calculate and implement a local threshold score based on current time of day and the threshold score model.

In a similar implementation, the remote computer system can assign global threshold scores to discrete rooms, areas, or room types (e.g., bedroom, bathroom, cafeteria, common interior space, common outdoor space, etc.) within the facility based on locations within the facility at which past fall events occurred. In particular, the system can assign lower global threshold scores to rooms, areas, and/or room types within the facility at which fall events have occurred with greater frequency in the past, thereby increasing sensitivity of the complete fall detection model to fall events in these locations, and vice versa.

In the foregoing implementation, the remote computer system can also: track the location of the wearable device over time, as described above; and return local threshold scores to the wearable device based on the wearable device's location as the resident moves throughout the facility.

However, the wearable device and the remote computer system can implement any other method or technique to dynamically adjust local and global threshold scores applied to outputs of the compressed and complete fall detection models to detect and then confirm fall events, respectively, based on any other biometric parameter, time-based parameter, or location-based parameter, etc.

10. Machine Learning

In one variation, the remote computer system: interfaces with a human (e.g., the resident and/or a care provider) to confirm true positive, true negative, false positive, and false negative fall events detected by compressed and complete fall detection models; labels sensor data collected from the wearable device accordingly; appends a training set with these labeled sensor data; and retrains the compressed and complete fall detection models on this training set. In particular, the remote computer system can: update the complete fall detection model based on labeled data received from deployed wearable devices in order to reduce false positive and false negative fall events determined by the complete fall detection model based on feedback provided by the resident through her wearable device and/or by a care provider through an incident report; similarly update the compressed fall detection model; and push this updated compressed fall detection model to deployed wearable devices.

For example, the remote computer system can refine the compressed fall detection model to reduce a false positive rate of fall events detected by a wearable device implementing the compressed fall detection model while maintaining a false negative rate of fall events at approximately null in order to: reduce a frequency with which the wearable device uploads sensor data to the remote computer system for reprocessing with the complete fall detection model, thereby extending battery life of the wearable device and decreasing resource load on the remote computer system to process possible fall events by other residents at the same or other facility; without increasing risk of failing to detect a fall event. The remote computer system can also refine the compressed and complete fall detection models to enable detection of a wider variety of fall modes, such as falls from standing, out of a chair, from leaning on a wall, from leaning on a table, from a walker, from a cane, etc. as sensor data representative of these fall pathways are collected and labeled by residents and/or care providers, as described below.

10.1 True Positive Confirmation by Care Provider

In this variation, the remote computer system can: extract verification of the fall event from the digital incident report completed by the care provider, such as through her assigned computing device during or after assisting the resident; label the corpus of sensor data (e.g., a subset of data packets within the corpus of sensor data received from the wearable device following local detection of the fall event) with verified fall event labels; append a training set with this corpus of labeled sensor data; and then retrain the complete fall detection model (and the compressed fall detection model) on this training set.

In this variation, the remote computer system can label data packets received from the wearable device with feedback received from a care provider dispatched to the resident and then retrain the complete fall detection model based on these labeled data. For example, when a care provider reaches a fallen resident after being dispatched by the remote computer system to handle the fall event, the care provider can manually confirm that she has reached the resident through her assigned computing device, or the remote computer system can cooperate with the care provider's computing device and a local wireless hub to automatically confirm that the care provider has reached the resident. The care provider can then manually confirm that the resident has fallen, such as by checking a fall event confirmation box within a care provider portal or within the incident report rendered on the care provider's computing device. The remote computer system can then: label a sequence of data packets received from the resident's wearable device responsive to detecting the fall event with positive feedback that the fall event occurred; add these labeled data packets to the training set; and retrain the complete and compressed fall detection models on this expanded training set.

10.2 False Positive Confirmation by Care Provider

Alternatively, upon arrival at the resident responsive to a fall response prompt, the care provider can determine that the resident has not fallen; the care provider can then indicate on the incident report or through the care provider portal that the resident did not fall. Upon receipt of such feedback from the care provider, the remote computer system can: label sensor data that triggered detection and confirmation of the fall event as not representative of a fall event; add these labeled data to the training set; and retrain the compressed and complete fall detection models on this expanded data set accordingly.

10.3 False Positive Confirmation by Resident

In another implementation, the remote computer system receives manual rejection of a fall event from the resident via her wearable device. For example, upon detecting a fall event in Block S120, the wearable device can: upload sensor data and a cue for confirmation of the fall event via a wireless hub to the remote computer system in Block S140; and issue an audible and/or visual alarm, such as by playing an audible alert through a speaker integrated into the wearable device, flashing a light inside the wearable device, and/or rendering a graphical fall warning on a display integrated into the wearable device. In this example, if the resident silences the fall alarm (e.g., by tapping and holding down on the input region of the computing device for a duration of four seconds), the wearable device can record this input as rejection of the fall event and can return this fall event rejection to the remote computer system via the wireless hub.

If the remote computer system has already broadcast a fall response prompt for the fall event to a computing device of a care provider at the facility, the remote computer system can deactivate the fall response prompt upon receipt of this rejection from the wireless hub. Alternatively, following receipt of rejection of the fall event by the resident, the remote computer system can deescalate the fall response prompt, such as by updating a prompt to the care provider dispatched to the resident's location to check on the resident rather than assist the resident directly. Rather than rush to the resident's location, the care provider can move toward the resident's location more casually to check that the resident is not in need of assistance. The care provider can then provide feedback to the remote computer system regarding the resident, such as confirmation that the resident has or has not fallen. The remote computer system can then label related sensor data and retrain the compressed and complete fall detection models accordingly. Further, if the care provider indicates that a fall event has occurred, the remote computer system can automatically return an incident report to the care provider's computing device for completion, as described above.

Therefore, the remote computer system can prioritize feedback received from the care provider over feedback received from the resident, such as by overwriting a fall event rejection received from the resident with fall event confirmation received from the care provider. Furthermore, the remote computer system can learn to reject fall event rejections received from a particular resident if the particular resident repeatedly rejects fall events detected by her assigned wearable device despite confirmation of these fall events by care providers responding to these fall events.

10.4 True Positive Confirmation by Resident

However, in the foregoing implementation, if the resident fails to silence the audible or visual alert output by her wearable device following detection of the fall event, such as within a preset threshold time of ten seconds following issuance of the alert, the remote computer system can interpret lack of rejection of this alert as confirmation of the fall event and process the fall response prompt accordingly in Block S170.

10.5 False Negative Detection by Remote Computer System

As described above, the wearable device can regularly offload contents of its buffer to the remote computer system via local wireless hubs, such as on a three-minute interval (e.g., a "buffer cycle") based on a length of the buffer. If the wearable device does not detect a fall event during a buffer cycle, the remote computer system can scan data received from the wearable device during the current buffer cycle for data packets that may be representative of a fall event. (Alternatively, the remote computer system can query the wearable device for contents of a second buffer of extended duration, such as one hour or one day, and scan data received from the wearable device during the current buffer cycle for data packets that may be representative of a fall event.) For example, the remote computer system can detect a contiguous sequence of data packets representing a relatively large rate of change in ambient pressure, representing relatively large accelerations, or representing accelerations approximating free-fall acceleration due to gravity in one direction followed by a rapid acceleration in a different direction. The remote computer system can then pass the particular data packet through the complete fall detection model to confirm that a fall event was not missed by the compressed fall detection model executing on the wearable device during the recent buffer cycle (i.e., a false negative fall event). The remote computer system can therefore asynchronously and selectively reprocess sensor data collected by the wearable device to confirm that the wearable device did not output a false negative fall event during the buffer cycle.

In this implementation, if the remote computer system detects and confirms a fall event during the current buffer cycle, the remote computer system can execute a fall response routine, as described above, to dispatch a care provider to a last known location of the wearable device in Block S170. Therefore, by reprocessing data received from the wearable device even when no fall event is detected by the wearable device, the remote computer system can detect a fall event by a resident and dispatch a care provider to aid the resident, though a delay up to a duration of the buffer may occur between the resident's fall and the time that the care provider is dispatched to assist the resident. In particular, the remote computer system can execute a deeper, more complex complete fall detection model—exhibiting a false negative rate less than that of the compressed fall detection model executing on the wearable device—in order to detect and handle true positive fall events not detected by the wearable device due to a less sophisticated nature of the compressed fall detection model limited by processing, memory, and power capabilities of the wearable device. The remote computer system can then implement methods and techniques described above to handle the detected fall event.

Furthermore, in this implementation, if the remote computer system confirms a fall event during the current buffer cycle, the remote computer system can modify or update the compressed fall detection model, such as described below, in order to enable the compressed fall detection model to detect such a fall event and to reduce false negative fall events output by the compressed fall detection model. In particular, the remote computer system can automatically label these data as representing a fall event responsive to manual confirmation of the fall event by the care provider via an incident report and then retrain the compressed fall detection model accordingly in order to reduce a false negative rate of the compressed fall detection model before pushing this updated compressed fall event model to deployed wearable devices, as described below. Alternatively, if the care provider confirms through the incident report that a fall event did not occur, the remote computer system can label these sensor data accordingly and retrain the complete fall detection model based on these new labeled data in order to reduce a false positive rate of the complete fall detection model.

10.6 False Negative Confirmation by Resident

In another implementation, the remote computer system and the wearable device interfaces with the resident to respond to a fall event not detected by the compressed fall detection model (i.e., a "false negative" fall event). In one example, if the resident falls while wearing the wearable device but the wearable device fails to detect this fall event from sensor data recorded as the resident falls, the resident can enter an input on the wearable device to indicate that she has fallen, such as by repeatedly tapping on the input region of the wearable device. In this example, the wearable device can record the resident's input(s) as a fall event and issue a fall alarm accordingly, such as by connecting to a local wireless hub in Block S130 and uploading the fall alarm, a request to dispatch a care provider to the wearable device's current location, and sensor data currently stored in the buffer to the local wireless hub in Block S140.

Once the fall alarm is received, the remote computer system can execute a fall response routine, as described above. For example, the remote computer system can: dispatch a care provider to assist the resident; serve an incident report and prompt to confirm the fall event involving the resident to the care provider; extract confirmation of the fall event from the incident report; and label sensor data accordingly before retraining the compressed and complete fall detection models. In this example, the remote computer system can: scan the sensor data received from the wearable device for a set of data packets most indicative of a fall event, as described above; label this set of data packets as true positive fall events based on confirmation of the fall event supplied by the care provider via the incident report (rather than by the resident, who may be less trustworthy or objective than the care provider); and retrain the complete fall detection model based on these labeled data in order to reduce the false negative rate of the compressed and complete fall detection models. (In this example, if a data packet likely representative of the fall event is not identified in the current set of data packets received from the wearable device, the remote computer system can also scan a set of data packets from a preceding buffer cycle received from the wearable device for a data packet likely representative of the fall event indicated by the resident.)

Therefore, the resident's computing device can transmit an alert and a corpus of sensor data from the buffer to a local wireless hub in response to receiving selection of an input region on the wearable device at a particular time, wherein the second corpus of sensor data includes sensor data recorded to the buffer by the wearable device up to the particular time. In response to receiving the alert, the remote computer system can: dispatch a care provider to assist the resident; access confirmation of the fall event, involving the resident, submitted by the care provider; scan the corpus of sensor data for a segment of sensor data exhibiting correlation to a fall; label the segment of sensor data with a fall event label; append a training set with the segment of sensor data; and retrain the complete fall detection model (and the compressed fall detection model) according to the training set.

10.7 False Negative Confirmation by Care Provider

In another implementation, upon finding a fallen resident, a care provider can submit a fall event to the remote computer system through her assigned computing device. For example, upon receipt of manual entry of a fall event, the care provider's computing device can automatically broadcast a beacon to connect with a nearest resident wearable device, download an ID from the wearable device, and upload the wearable device ID with a fall alarm to the remote computer system. Alternatively, the care provider can manually enter a resident number, resident name, or other resident identifier into the application executing on her computing device in order to link the fall event to the correct resident.

Upon receipt of a manual fall event prompt from the care provider, the remote computer system can implement methods and techniques described above to: serve an incident response to the care provider's computing device for manual completion, such as confirmation of the fall event and an approximate time of the fall event; select a contiguous sequence of data packets recorded by the resident's wearable device proximal the care provider's suggested time of the fall event and containing signals indicative of a fall event; label this sequence of data packets with a confirmed fall event; and retrain the complete fall detection model accordingly in order to reduce a false negative rate of the complete fall detection model. The remote computer system can similarly retrain the compressed fall detection model.

10.8 Retraining

The remote computer system can therefore: collect feedback—regarding occurrence or lack of fall events involving residents—from residents, care providers, and/or any other individuals or entities affiliated with the facility during a normal course of operation of the facility over time; automatically label (i.e., annotate) sensor data received from wearable devices based on these feedback; and aggregate these labeled data into a training set. By regularly retraining the complete fall detection model over time based on updated training sets, the remote computer system can improve the precision of the complete fall detection model, including reducing false positive and false negative rates of the complete fall detection model. The remote computer system can then compress the complete fall detection model to a memory footprint suitable for execution on a resident's wearable device (or separately retrain the compressed fall detection model on the updated training set) and can distribute (e.g., push) the updated compressed fall detection model to wearable devices assigned to residents of the facility via a computer network and local wireless hubs arranged throughout the facility. For example, the remote computer system can calculate new compressed and complete fall detection models regularly (e.g., once per month) or once labeled sensor data for a target number of (e.g., 100) new fall events is collected.

In the implementation described above in which the complete fall detection model includes an artificial neural network, the remote computer system can recalculate weights of connections between neurons or otherwise reprioritize neurons in the neural network each time the complete fall detection model is updated. The remote computer system can then generate a new compressed fall detection model, such as by compiling the highest-weight connections and corresponding neurons into an updated compressed fall detection model requiring a memory footprint of a size supported by the wearable device. In particular, as the remote computer system updates the complete fall detection model over time based on data packets and corresponding labels (i.e., feedback from residents and/or care providers) received from deployed wearable devices, the remote computer system can generate an updated compressed fall detection model accordingly and queue this updated compressed fall detection model for distribution to these deployed wearable devices. For example, when a wearable device is subsequently active, wirelessly connected to a local wireless hub, and is not worn by a resident (e.g., such as determined by the skin temperature sensor reading a skin temperature below a threshold temperature of 94° F.), the wearable device can download a copy of the updated compressed fall detection model from the remote computer system and replace an older compressed fall detection module with this updated fall detection model.

Alternatively, the complete and compressed fall detection models can contain static sets of neurons and layers, and the remote computer system can: recalculate weights of connections between neurons in the complete fall detection model based on label data packets received from deployed wearable devices; populate a table with a subset of these recalculated weights (e.g., the highest weights in the complete fall detection model); and queue the table for distribution to deployed wearable devices. Upon receipt of this table, a wearable device can update weights of connections in a copy of the compressed fall detection model stored locally based on values contained in this table.

However, the remote computer system can implement any other methods or techniques to retrain or update the complete and compressed fall detection models based on data and feedback received from deployed wearable devices and from residents and care providers, respectively.

11. Pre-Fall Activity

In one variation, the wearable device can also classify actions or activities performed by a resident wearing the wearable device throughout operation of the wearable device, as shown in FIG. 1. For example, the wearable device can pass sequences of data packets through an action classifier stored locally on the wearable device to determine actions (e.g., walking, walking while assisted by a roller, sitting, running, sleeping, eating, standing, skipping, etc.) performed by the resident. In this variation, when the wearable device determines that the resident has fallen in Block S120, the wearable device can upload a last action performed by the resident prior to a fall event to the wireless hub in addition to a fall alarm and request for confirmation of the fall event in Block S140. The remote computer system can thus link this action to the resident's fall in Block S180. Over time, the remote computer system can amass records of fall events by residents and corresponding actions leading up to fall events, and the remote computer system can analyze these data to identify a particular action correlated with a higher incidence of falls by all residents, by residents within a particular facility, by residents consuming a particular medication, by residents diagnosed with a particular disease or disorder, and/or by residents of a particular demographic, etc. The remote computer system can then supply this correlation between the particular action and fall events to a facility administrator or other representative, such as in the form of a recommendation to limit the particular action across residents at the facility or among a subset of residents at the facility.

12. Fall Detection Layers

In one variation, the complete and/or compressed fall detection models incorporate additional device-specific and/or demographic-specific layers in order to tailor these fall detection models to a particular wearable device assigned to a resident and/or to a particular characteristic of the resident, as shown in FIG. 2.

In one example, the system generates a generic compressed fall detection model and loads instances of this generic compressed fall detection model onto smartphones, tablets, wearable devices, and/or devices of various other types assigned to, carried by, or worn by residents of the facility. The system can also selectively load device-specific layers onto these devices based on a make, model, operating system, and/or other characteristic of each device. In this example, a device-specific layer can function to normalize, filter, or otherwise preprocess sensor data collected by sensors integrated into a device executing the generic compressed fall detection model thereby conditioning these sensor data for insertion into the generic compressed fall detection model. In particular, the system can implement device-specific layers to prepare data for application to the generic compressed fall detection model in order to maintain sufficient precision of the generic compressed fall detection model despite differences in sensor ranges, sensor orientations, sensor sensitivities, sampling characters, etc. of different devices executing the same generic compressed fall detection model.

In another example, the system can distribute demographic-specific layers to devices associated with residents subscribed to the system. For example, over time, the system can extrapolate differences in fall motions across various demographics and can generate demographic-specific layers for these various demographics. In this example, the system can distribute: a Parkinson's layer to a wearable device assigned to a resident suffering from Parkinson's disease; a paraplegic layer to a wearable device assigned to a paraplegic resident; female-specific and male-specific layers to wearable devices assigned to female and male residents, respectively; a diabetes layer to a wearable device assigned to a resident suffering diabetes; and an obesity layer to a wearable device assigned to an obese resident; etc. Like a device-specific layer, a demographic-specific layer functions to tailor a generic compressed fall detection model to motions common to or characteristic of a subset of residents associated with the corresponding demographic. In particular, a resident of a particular demographic may fall differently or may be more susceptible to a particular fall mode than a resident of a different demographic. The system can therefore load a particular demographic-specific layer onto a resident's wearable device (or other device) based on demographic or diagnosis data of the resident, such as stored in a medical record. For example, the system can scan resident medical records for existing and new diagnoses and automatically queue demographic-specific layers for distribution to wearable devices assigned to corresponding residents.

Alternatively, the remote computer system can implement similar methods and techniques to generate alternate device-specific and/or demographic-specific complete and/or compressed fall detection models tailored to a particular device used by a resident and/or to a particular characteristic of the resident.

The wearable device and/or the remote computer system can implement similar methods and techniques to identify and handle other "activities of daily living" (or "ADL") (e.g., eating, bathing, dressing, toileting, transferring, and continence). For example, the wearable device can pass data packets into the compressed fall detection model, as described above, and the compressed fall detection model can output a vector that indicates walking, falling, running, swimming, etc. and a fall event flag for the resident as is relevant. The wearable device and the remote computer system can also implement similar methods and techniques to trigger other actions or alerts in response to a fall or other ADL.

13. Fall Detection at Local Wireless Hub

In one variation described above and shown in FIG. 4, a local wireless hub executes an intermediate fall detection model to confirm a fall event involving a resident upon receipt of sensor data and a cue to retest these sensor data from a wearable device assigned to the resident. In particular, the remote computer system can implement methods and techniques described above to generate and maintain an intermediate fall detection model representing an abbreviated form of the complete fall detection model and sized for memory and processing capacities of local wireless hubs deployed to the facility. For example, the intermediate fall detection model can be characterized by an intermediate memory footprint greater than the memory footprint of the compressed fall detection model and smaller than the memory footprint of the complete fall detection model. The remote computer system can distribute the intermediate fall detection model to local wireless hubs throughout the facility and regularly serve updates for the intermediate fall detection model to these local wireless hubs over time, such as a via a computer network (e.g., the Internet). A local wireless hub can thus implement methods and techniques described above to pass sensor data received from the wearable device though the intermediate fall detection model to confirm a fall event initially detected by the wearable device. If the intermediate fall detection model outputs confirmation of the fall event (e.g., if a fall event confidence score output by the intermediate fall detection model exceeds an intermediate threshold score), the local wireless hub can return these sensor data back to the remote computer system for further processing, as described above. Therefore, the local wireless hub can implement deeper, more complex logic to confirm a fall event initially detected by the wearable device before transmitting data collected from the resident to the remote computer system, which may be located physically outside of the facility, thereby maintaining privacy of the resident as an inverse function of perceived risk to the resident.

In a similar variation, upon receipt of sensor data and a cue to retest these sensor data, the local wireless hub can attempt connection to a remote computer system via a computer network (e.g., the Internet) and then transmit the corpus of sensor data to the remote computer system upon establishing connection to the remote computer system. However, if a local area network or wireless network is currently down, malfunctioning, oversubscribed, or exhibiting low bandwidth or upload speeds or if the local wireless hub otherwise fails to establish a suitable connection to the remote computer system, the local wireless hub can withhold these sensor data from the remote computer system and instead pass these sensor data through the intermediate fall detection model to locally confirm the fall event, thereby enabling the system to rapidly confirm the fall event locally rather than delay confirmation of the fall event until a connection to the remote computer system can be reestablished. Following local confirmation of the fall event, the local wireless hub can locally execute a fall event handling routine, as described above, to transmit a prompt to assist the resident to a computing device affiliated with a care provider in the facility, such as through a local wireless network.

However, the local wireless hub can implement any other method or techniques to confirm a fall event—initially detected by a wearable device—before passing sensor data back to the remote computer system for further processing or before locally executing a fall event handling routine.

14. Multiple Wearable Devices

Figure 5A:
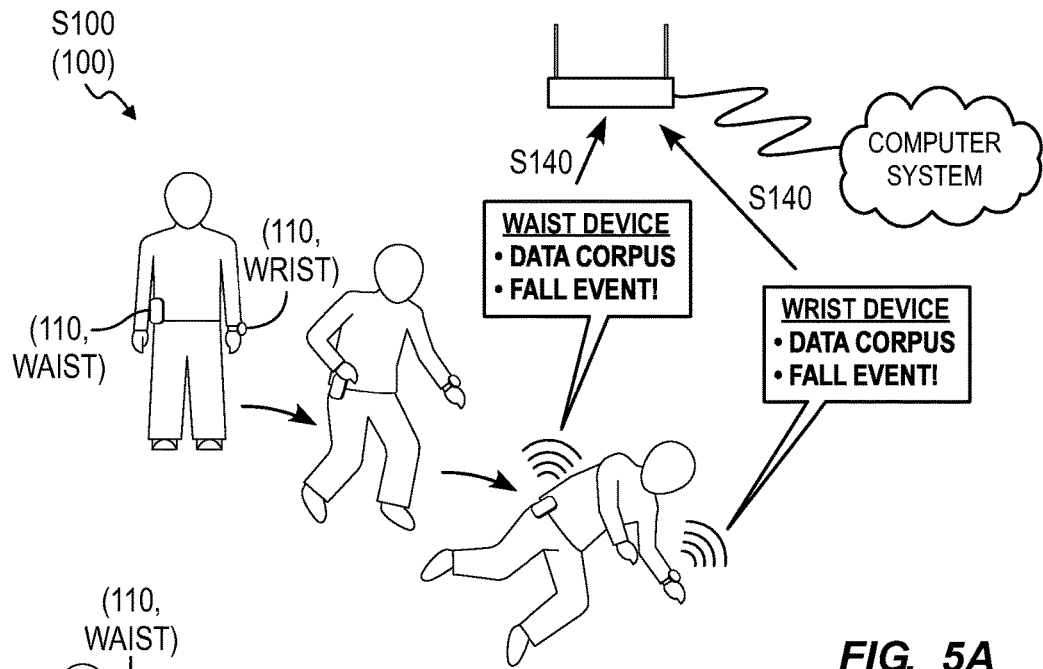
FIGS. 5A and 5B are flowchart representations of one variation of the method.
Figure 5B:
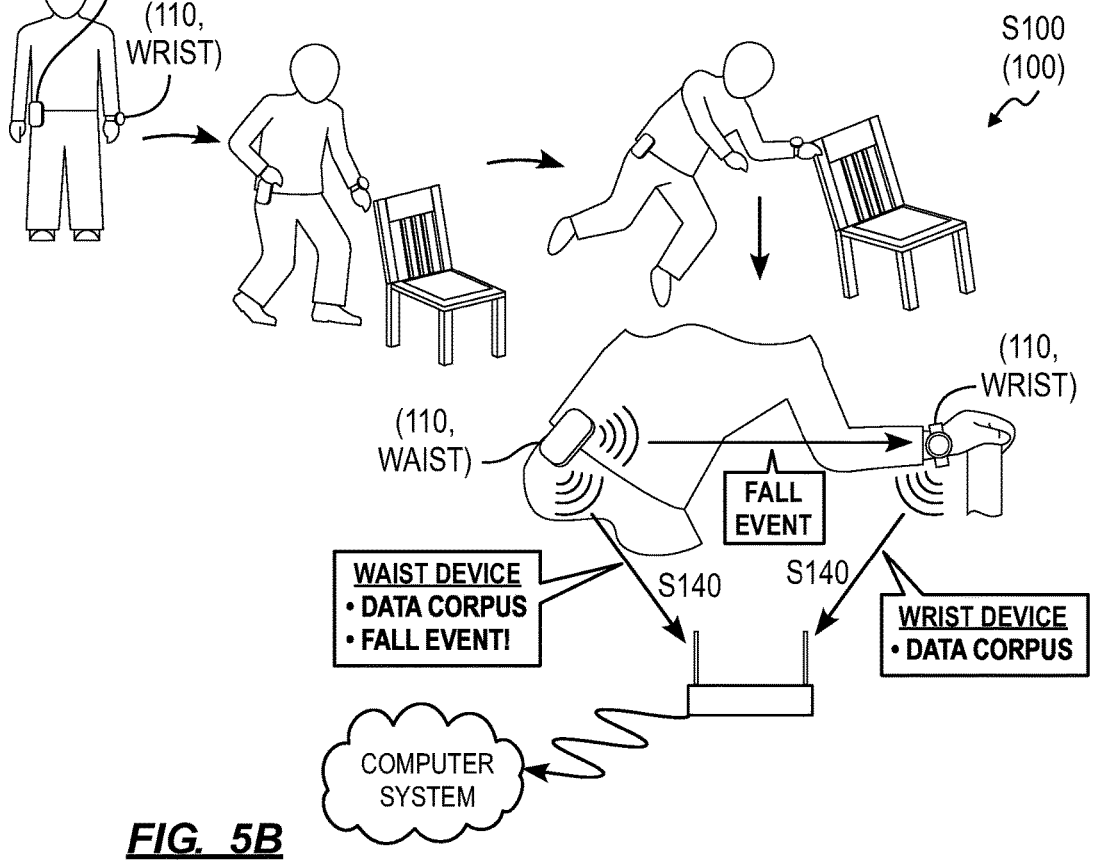

In another variation shown in FIGS. 5A and 5B, the system includes multiple devices assigned to a resident and simultaneously worn or carried by the resident, wherein each device: includes a set of internal sensors; reads sensor data from these internal sensors; passes these sensor data through a compressed fall detection model to detect a fall event; and uploads these sensor data and a cue to retest these sensor data when a fall event is detected, as described above. For example, the system can include: the wearable device configured to be worn on a wrist; a second device defining a brooch format configured to be worn around the neck; a third device configured to clip to a belt or pant waist line; and a native application executing methods and techniques described above on a smartphone carried by a resident; etc. In this example, each device can implement methods and techniques described above to independently collect sensor data, to detect a fall event based on these data, and to upload these data to the remote computer system for further processing.

In one implementation, a device—in the set of devices worn or carried by a resident—can implement a compressed fall detection model customized for a configuration of the device (e.g., a position on a human body on which the device is designed to be worn) and a sensor suite integrated into the device. Upon detecting a fall event, the wearable device can upload sensor data from its buffer and a cue to retest these sensor data for a fall event to a local wireless hub, as described above. Upon receipt of these data from the device, the hub can—automatically or when triggered by the remote computer system—query other devices assigned to the same resident for contents of their buffers. The remote computer system can then pass sensor data from each of the distinct devices—worn or carried on different locations on the resident's body—through a complete multi-device fall detection model to confirm the fall event. In particular, by merging sensor data from multiple discrete devices worn or carried on the resident, the remote computer system can confirm or reject the fall event with a greater degree of accuracy. For example, the remote computer system may confirm fall events characteristic of different fall modes in which the resident holds a wall, walker, cane, table, or chair (shown in FIG. 5B) while falling or reaches outwardly to brace herself against impact with a floor during free fall (shown in FIG. 5A) by analyzing motion data collected from both a wearable device arranged on one of the resident's wrists and another device connected to the resident's waistband or belt, both of which may independently collect insufficient motion data to accurately enable a compressed fall detection model to detect all of these fall event modes. The remote computer system can then execute a fall event handling routine, as described above, once the fall event is confirmed.

In another implementation shown in FIG. 5B, once one device arranged on the resident detects a fall event, the device can wirelessly transmit sensor data and a cue to retest these sensor data to a master device arranged on the resident (e.g., the wearable device). Upon receipt of the cue from the device, the master device can query each other device arranged on the resident for recent sensor data; pass these sensor data from multiple discrete devices through a compressed multi-device fall detection model to calculate one confidence score for recent occurrence of a fall event involving the resident; and then push these sensor data (or trigger the devices to push these sensor data) to a local wireless hub if the confidence score exceeds a threshold score. Similarly, if the master device (e.g., the wearable device) detects a fall event, the master device can, transmit a prompt to each other device arranged on the resident to return sensor data contained in buffers stored on these other devices: to the master device for local processing with the compressed multi-device fall detection model; directly to the local wireless hub for remote processing with the complete multi-device fall detection model. The remote computer system (or the local wireless hub) can then implement methods and techniques described above to pass these data through a complete multi-device fall detection model to confirm the fall event.

However, the systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for detecting and responding to falls by residents within a facility, the method comprising:
   at a wearable device worn by a resident:
      writing sensor data from a sensor integrated into the wearable device to a buffer;
      inputting sensor data read from the sensor into a compressed fall detection model, the compressed fall detection model comprising a first neural network, defining a first quantity of nodes, to calculate a first confidence score for occurrence of a fall event at the wearable device at a first time, characterized by a first memory footprint, stored locally on the wearable device, and defining a compressed form of a complete fall detection model;
      in response to the first confidence score exceeding a local threshold score:
         detecting a fall event at the wearable device;
         wirelessly connecting to a local wireless hub;
         transmitting a corpus of sensor data from the buffer and a cue for automated confirmation of the fall event to the local wireless hub, the corpus of sensor data recorded over a duration of time extending up to approximately the first time; and
         disconnecting from the local wireless hub;
   at a remote computer system:
      inputting the corpus of sensor data into the complete fall detection model, the complete fall detection model comprising a second recurrent neural network, defining a second quantity of nodes greater than the first quantity of nodes, to calculate a second confidence score for occurrence of the fall event at the wearable device at the first time, defining a second memory footprint greater than the first memory footprint, and stored remotely from the wearable device; and
      in response to the second confidence score exceeding a global threshold score:
         confirming the fall event at the wearable device; and
         dispatching a care provider to assist the resident.

2. The method of claim 1, further comprising, at the wearable device:
   tracking a step rate of the resident based on motion data read from an inertial sensor integrated into the wearable device;
   tracking a skin temperature of the resident based on temperature values read from a temperature sensor integrated into the wearable device; and
   setting the local threshold score as an inverse function of step rate and deviation of skin temperature of the resident from a target skin temperature.

3. The method of claim 1, further comprising:
   calculating a frequency of historical fall events, stored in a fall event database, across a group of residents as a function of time of day; and
   setting the global threshold score as an inverse function of frequency of historical fall events at a current time of day.

4. The method of claim 1:
   further comprising:
      at the wearable device, broadcasting a beacon signal;
      calculating a location of the resident based on a known location of the local wireless hub within the facility in response to receipt of the beacon signal from the wearable device at the local wireless hub;
   wherein dispatching the care provider to assist the resident comprises:
      generating a notification comprising a prompt to assist the resident;
      inserting a pointer to the location into the notification; and
      transmitting the notification to a computing device affiliated with the care provider.

5. The method of claim 4:
   wherein writing sensor data to the buffer comprises writing motion data read from an accelerometer and a gyroscope, integrated into the wearable device, to the buffer defining a duration of multiple minutes; and
   wherein broadcasting the beacon signal comprises broadcasting the beacon signal multiple times per minute.

6. The method of claim 4, further comprising:
   at the wearable device, outputting an audible alarm at a second time in response to detecting the fall event;
   at the remote computer system:
      verifying the fall event at the wearable device in response to failure of the resident to clear the alarm within a threshold duration following the second time at the wearable device; and
      deescalating a priority of the notification at the computing device in response to receipt of an input to clear the alarm within the threshold duration following the second time at the wearable device.

7. The method of claim 1, further comprising, at the local wireless hub:
   attempting connection to a remote computer system via a computer network;
   in response to establishing connection to the remote computer system, transmitting the corpus of sensor data to the remote computer system; and in response to failing to establish connection to the remote computer system:
   inputting the corpus of sensor data into an intermediate fall detection model to confirm the fall event, the intermediate fall detection model stored on the local wireless hub, defining a second abbreviated form of the complete fall detection model, and characterized by an intermediate memory footprint between the first memory footprint of the compressed fall detection model and the second memory footprint of the complete fall detection model; and
   in response to confirming the fall event, transmitting a local prompt to assist the resident, through a local wireless network, to a computing device affiliated with the care provider.

8. The method of claim 1, further comprising:
at the remote computer system:
   generating the complete fall detection model characterized by the second memory footprint;
   generating an intermediate fall detection model representing an abbreviated form of the complete fall detection model and characterized by an intermediate memory footprint between the first memory footprint of the compressed fall detection model and the second memory footprint of the complete fall detection model;
   generating the compressed fall detection model characterized by the first memory footprint less than the second memory footprint;
   distributing the intermediate fall detection model to the local wireless hub via a computer network; and
   distributing the compressed fall detection model to the wearable device via the computer network;
at the local wireless hub:
   in response to receiving the corpus of sensor data from the wearable device, inputting the corpus of sensor data into the intermediate fall detection model to detect the fall event; and
   in response to detecting the fall event, returning the corpus of sensor data to the remote computer system executing the complete fall detection model to confirm the fall event.

9. The method of claim 1:
wherein inputting sensor data into the compressed fall detection model comprises:
   calculating the first confidence score for occurrence of the fall event at the wearable device at the first time based on:
      a change in ambient pressure values, read from an ambient pressure sensor integrated into the wearable device over the duration of time; and
      similarity of motion data, read from an accelerometer and a gyroscope integrated into the wearable device over the duration of time, to a motion pattern of a fall represented in the compressed fall detection model; and
wherein writing sensor data to the buffer comprises writing ambient pressure values read from the ambient pressure sensor and motion data read from the accelerometer and the gyroscope to the buffer; and
wherein transmitting the corpus of sensor data to the local wireless hub comprises transmitting ambient pressure values and motion data to the local wireless hub in response to the confidence score exceeding the local threshold score.

10. The method of claim 1:
wherein writing sensor data into the wearable device to the buffer comprises writing sensor data to the buffer stored locally on the wearable device worn on a wrist of the resident;
further comprising, in response to detecting the fall event at the wearable device, transmitting a prompt to a second wearable device arranged on the resident to transmit sensor data contained in a second buffer stored on the second wearable device to the local wireless hub; and
wherein inputting the corpus of sensor data into the complete fall detection model remotely from the wearable device to confirm the fall event comprises confirming the fall event remotely from the wearable device and the second wearable device based on the corpus of sensor data received from the wearable device and sensor data received from the second wearable device.

11. The method of claim 1:
wherein dispatching the care provider to assist the resident comprises:
   accessing a digital incident report;
   inserting a name of the resident, affiliated with the wearable device, into the digital incident report;
   inserting a prompt to verify the fall event into the digital incident report; and
   transmitting the digital incident report to a computing device affiliated with the care provider; and
further comprising:
   extracting verification of the fall event from the digital incident report completed by the care provider at the computing device;
   labeling the corpus of sensor data with verified fall event labels;
   appending a training set with the corpus of sensor data; and
   retraining the complete fall detection model on the training set.

12. The method of claim 11, further comprising, in response to retraining the complete fall detection model:
   retraining the compressed fall detection model on the training set, the compressed fall detection model exhibiting a compressed memory footprint smaller than a complete memory footprint of the complete fall detection model; and
   pushing an update for the compressed fall detection model to the wearable device via a computer network.

13. The method of claim 1, further comprising:
at the wearable device, transmitting an alert and a second corpus of sensor data from the buffer to the local wireless hub in response to receiving selection of an input region on the wearable device at a second time, the second corpus of sensor data different from the first corpus of sensor data and comprising sensor data recorded to the buffer by the wearable device up to the second time;
remotely from the wearable device:
   in response to receiving the alert, dispatching a second care provider to assist the resident;
   accessing confirmation of a second fall event, involving the resident, submitted by the second care provider;
   scanning the second corpus of sensor data for a segment of sensor data exhibiting correlation to a fall;
   labeling the segment of sensor data with a fall event label;
   appending a training set with the segment of sensor data; and retraining the complete fall detection model according to the training set.

14. The method of claim 1:
wherein writing sensor data to the buffer comprises writing sensor data to the buffer defining a first duration;
further comprising:
at the wearable device, writing a second corpus of sensor data to a second buffer defining a second duration greater than the first duration;
remotely from the wearable device:
at a second time, receiving verification of a second fall event from a second care provider, the second fall event involving the resident and undetected by the wearable device;
querying the wearable device for contents of the second buffer;
scanning the second corpus of sensor data, received from the wearable device, for a segment of sensor data exhibiting correlation to a fall;
labeling the segment of sensor data with a fall event label;
appending a training set with the segment of sensor data; and
retraining the complete fall detection model according to the training set.

15. A method for detecting and responding to falls by residents within a facility, the method comprising:
at a wearable device worn by a resident:
writing sensor data from a sensor integrated into the wearable device to a buffer;
inputting sensor data read from the sensor into a compressed fall detection model to detect a fall event at the wearable device at a first time, the compressed fall detection model comprising a first neural network, defining a first quantity of nodes, to calculate a first confidence score for occurrence of a fall event at the wearable device at a first time, characterized by a first memory footprint, defining a compressed form of a complete fall detection model, and stored locally on the wearable device;
in response to detecting the fall event at the wearable device:
detecting a fall event at the wearable device;
wirelessly connecting to a local wireless hub;
transmitting a corpus of sensor data from the buffer and a cue for automated confirmation of the fall event to the local wireless hub, the corpus of sensor data recorded over a duration of time extending up to approximately the first time; and
disconnecting from the local wireless hub;
in response to the wearable device detecting the fall event, issuing a fall alarm for a care provider to assist the resident;
remotely from the wearable device:
inputting the corpus of sensor data into the complete fall detection model to verify the fall event at the wearable device at the first time, the complete fall detection model comprising a second recurrent neural network, defining a second quantity of nodes greater than the first quantity of nodes, to calculate a second confidence score for occurrence of the fall event at the wearable device at the first time, defining a second memory footprint greater than the first memory footprint and stored remotely from the wearable device; and in response to failure to verify the fall event at the wearable device based on the corpus of sensor data and the complete fall detection model, clearing the fall alarm.

16. The method of claim 15, further comprising:
at the wearable device, transmitting an alert and a second corpus of sensor data from the buffer to the local wireless hub in response to receiving selection of an input region on the wearable device at a second time, the second corpus of sensor data different from the first corpus of sensor data and comprising sensor data recorded to the buffer by the wearable device up to the second time;
remotely from the wearable device:
in response to receiving the alert, dispatching a second care provider to assist the resident;
accessing confirmation of a second fall event, involving the resident, submitted by the second care provider;
scanning the second corpus of sensor data for a segment of sensor data exhibiting correlation to a fall;
labeling the segment of sensor data with a fall event label;
appending a training set with the segment of sensor data; and
retraining the complete fall detection model according to the training set.

17. The method of claim 15, further comprising, at the local wireless hub:
attempting connection to a remote computer system via a computer network
in response to establishing connection to the remote computer system, transmitting the corpus of sensor data to the remote computer system; and
in response to failing to establish connection to the remote computer system:
inputting the corpus of sensor data into an intermediate fall detection model to confirm the fall event, the intermediate fall detection model stored on the local wireless hub, defining a second abbreviated form of the complete fall detection model, and characterized by an intermediate memory footprint between the first memory footprint of the compressed fall detection model and the second memory footprint of the complete fall detection model; and
in response to confirming the fall event, transmitting a local prompt to assist the resident, through a local wireless network, to a computing device affiliated with the care provider.

18. A method for detecting and responding to falls by residents within a facility, the method comprising:
at a wearable device worn by a resident:
writing sensor data from a sensor integrated into the wearable device to a buffer on a first time interval;
transmitting contents of the buffer to a local wireless hub on a second time interval longer than the first time interval;
on a third time interval shorter than the second time interval, scanning sensor data read from the sensor for fall events based on a compressed fall detection model, the compressed fall detection model comprising a first neural network, defining a first quantity of nodes, to calculate a first confidence score for occurrence of a fall event at the wearable device at a first time, characterized by a first memory footprint, defining a compressed form of a complete fall detection model, and stored locally on the wearable device;

in response to detecting a first fall event at a first time:
   wirelessly connecting to a local wireless hub;
   transmitting a first corpus of sensor data currently stored on the buffer and a cue for automated confirmation of the first fall event to the local wireless hub at approximately the first time; and
   disconnecting from the local wireless hub;
in response to the wearable device detecting the first fall event, issuing a fall alarm for a care provider to assist the resident at approximately the first time;
remotely from the wearable device:
   scanning the first corpus of sensor data for verification of the first fall event based on the complete fall detection model, the complete fall detection model comprising a second neural network, defining a second quantity of nodes greater than the first quantity of nodes, to calculate a second confidence score for occurrence of the fall event at the wearable device at the first time, defining a second memory footprint greater than the first memory footprint, and stored remotely from the wearable device; and
   in response to failure to verify the first fall event based on the first corpus of sensor data and the complete fall detection model, clearing the fall alarm at approximately the first time.

19. The method of claim 18, further comprising, remotely from the wearable device:
- in response to receipt of a second corpus of sensor data from the buffer of the wearable device on the second time interval sans detection of a fall event by the wearable device at a second time, scanning the second corpus of sensor data for a second fall event based on the complete fall detection model; and
- in response to detecting the second fall event, issuing a second fall alarm for a care provider to assist the resident at approximately the second time.

\* \* \* \* \*